United States Patent [19]
Maruta et al.

[11] Patent Number: 5,976,856
[45] Date of Patent: *Nov. 2, 1999

[54] RECOMBINANT THERMOSTABLE ENZYME WHICH FORMS NON-REDUCING SACCHARIDE FROM REDUCING AMYLACEOUS SACCHARIDE

[75] Inventors: Kazuhiko Maruta; Michio Kubota; Toshiyuki Sugimoto, all of Okayama, Japan

[73] Assignee: Kabushiki Kaisha Hayashibara Seibutsu Kagaku Kenkyujo, Okayama, Japan

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/505,448

[22] Filed: Jul. 21, 1995

[30] Foreign Application Priority Data

Jul. 21, 1994 [JP] Japan ..................................... 6-190183
Jul. 4, 1995 [JP] Japan ..................................... 7-189706

[51] Int. Cl.⁶ .............................. C12N 9/26; C12N 9/10; C12N 9/34
[52] U.S. Cl. ......................... 435/201; 435/200; 435/205; 435/193; 435/96; 435/97; 435/99; 435/101
[58] Field of Search ..................................... 435/200, 201, 435/205, 96, 97, 99, 101, 193

[56] References Cited

U.S. PATENT DOCUMENTS

| 4,521,252 | 6/1985 | Miyake et al. | 127/46.3 |
| 5,714,368 | 2/1998 | Nakada et al. | 435/201 |
| 5,723,327 | 3/1998 | Ikegami et al. | 435/201 |

FOREIGN PATENT DOCUMENTS

| 0 688 867 | 12/1995 | European Pat. Off. . |
| 0688866 | 12/1995 | European Pat. Off. . |
| 50-1544858 | 12/1975 | Japan . |
| 58-23799 | 2/1983 | Japan . |
| 58-72598 | 4/1983 | Japan . |
| 58-216695 | 12/1983 | Japan . |
| 2106912 | 8/1982 | United Kingdom . |

OTHER PUBLICATIONS

Lama, Licia et al., "Thermostable amylolytic activity from *Sulfolobus solfataricus.*" Biotech Forum Europe, vol. 8, No. 4, pp. 201–203 (1991).

Lama, Licia et al., "Starch conversion with immobilized thermophilic archeabacterium *Sulfolobus solfatarious.*", Biotechnology Letters, vol. 12, No. 6, pp. 431–432 (Jun. 1990).

Sambrook et al., *Molecular Cloning: A Laboratory Manual;* Cold Spring Harbour Labratory Press; pp. v–xxxii; 1989.

Southern, E.M.; "Detection of Specific Sequences Among DNA Fragments Separated by Gel Electrophoresis."; Journal of Molecular Biology; vol. 98; pp. 503–571; 1975.

The Amylase Research Society of Japan, editors; *Handbook of Amylases and Related Enzymes: Their Sources, Isolation Methods, Properties and Applications.* Permagon Press; pp. xi–81; 1988.

*Primary Examiner*—Rebecca E. Prouty
*Attorney, Agent, or Firm*—Browdy & Neimark

[57] ABSTRACT

Disclosed is a recombinant thermostable enzyme which has a molecular weight of about 69,000–79,000 daltons and a pI of about 5.4–6.4, and forms non-reducing saccharides having a trehalose structure as an end unit from reducing amylaceous saccharides having a degree of glucose polymerization of at least 3. The enzyme has satisfactorily high thermostability, i.e. it is substantially not inactivated even when incubated in an aqueous solution (pH 7.0) at 85° C. for 60 min, and this facilitates the production of such non-reducing saccharides on an industrial scale and in a satisfactorily-high yield.

1 Claim, 6 Drawing Sheets

RECOMBINANT THERMOSTABLE ENZYME WHICH FORMS NON-REDUCING SACCHARIDE FROM REDUCING AMYLACEOUS SACCHARIDE

BACKGROUND OF THE INVENTION

1. Field of the Invention

The present invention relates to a recombinant enzyme which forms non-reducing saccharides having a trehalose structure as an end unit from reducing amylaceous saccharides having a degree of glucose polymerization of at least 3.

2. Description of the Prior Art

Trehalose is a disaccharide which consists of 2 glucose molecules that are linked together with their reducing groups, and, naturally, it is present in fungi, algae, insects, etc., in an extremely small quantity. Having no reducing residue within the molecule, trehalose does not cause an unsatisfactory browning reaction even when heated in the presence of amino acids or the like, and because of this it can advantageously sweeten food products without fear of causing unsatisfactory coloration and deterioration. Trehalose, however, could not have been readily prepared in a desired amount by conventional production methods, so that it has not scarcely been used for sweetening food products.

Conventional production methods are roughly classified into 2 groups, i.e. the one using cells of microorganisms and the other using a multi-enzymatic system where several enzymes are allowed to act on saccharides. The former, as disclosed in Japanese Patent Laid-Open No.154,485/75, is a method which comprises growing microorganisms such as bacteria and yeasts in nutrient culture media, and collecting trehalose mainly from the proliferated cells. The latter, as disclosed in Japanese Patent Laid-Open No.216,695/83, is a method which comprises providing maltose as a substrate, allowing a multi-enzymatic system using maltose- and trehalose-phosphorylases to act on maltose, and recovering the formed trehalose from the reaction system. The former facilitates the growth of microorganisms, but has a demerit that the content in the microorganisms is at most 15 w/w %, on a dry solid basis (d.s.b.). Although the latter can readily separate trehalose, it is theoretically difficult to increase the trehalose yield by allowing such enzymes to act on substrates at a considerably-high concentration because the enzymatic reaction in itself is an equilibrium reaction of 2 different types of enzymes and the equilibrium point constantly inclines to the side of forming glucose phosphate.

In view of the foregoing, the present inventors energetically screened enzymes which form non-reducing saccharides having a trehalose structure from amylaceous saccharides having a degree of glucose polymerization of at least 3, and have found that microorganisms such as those of the genera Rhizobium and Arthrobacter produce an absolutely novel enzyme which forms such non-reducing saccharides from such reducing amylaceous saccharides. They disclosed such an enzyme in Japanese Patent Application No.349,216/93. They also found that trehalose is readily formed from such non-reducing saccharides when glucoamylase or α-glucosidase acts on them.

It was found that the enzymes produced from the aforesaid microorganisms have an optimum temperature of about 40° C., and have some difficulties in their thermostability when used to prepare trehalose. It is recognized in this field that the recommendable temperature in the saccharification reaction of starch or amylaceous saccharides is one which exceeds 55° C. because the contamination of microorganisms will occur at a temperature of 55° C. or lower, decrease the pH of the reaction mixtures, and inactivate the enzymes used. Thus, a relatively-large amount of substrates remain intact. While the use of enzymes with a poor thermostability, a great care should be taken to control the pH, and, when the pH level lowers to extremely low level, alkalis should be added to reaction mixtures to increase the pH level as quickly as possible.

In view of the foregoing, the present inventors screened thermostable enzyme with such a novel enzyme activity and have found that enzymes produced from microorganisms of the genus Sulfolobus including *Sulfolobus acidocaldarius* (ATCC 33909) are not substantially inactivated even when incubated at a temperature exceeding 55° C., and they efficiently produce such non-reducing saccharides having a trehalose structure as an end unit from reducing amylaceous saccharides. These micro-organisms, however, are not sufficient in the enzyme productivity, and this requires a relatively-large scale culture to industrially produce non-reducing saccharides having a trehalose structure as an end unit.

Recently, the recombinant DNA technology has made a remarkable progress. At present, even an enzyme whose total amino acid sequence has not been revealed can be readily prepared in a desired amount, if once a gene encoding the enzyme is isolated and the base sequence is decoded, by preparing a recombinant DNA containing a DNA that encodes the enzyme, introducing the recombinant DNA into microorganisms or cells of plants or animals, and culturing the resultant transformants. Under these circumstances, urgently required are to find a gene that encodes the thermostable enzyme and to decode the base sequence.

SUMMARY OF THE INVENTION

It is an object of the present invention to provide a recombinant thermostable enzyme which forms non-reducing saccharides having a trehalose structure as an end unit from reducing amylaceous saccharides with a degree of glucose polymerization of at least 3 by using the recombinant DNA technology.

It is a further object of the present invention to provide a DNA which encodes the recombinant thermostable enzyme.

It is yet another object of the present invention to provide a replicable recombinant DNA which contains the DNA.

It is another object of the present invention to provide a transformant into which the recombinant DNA is introduced.

It is yet another object of the present invention to provide a process for preparing the recombinant thermostable enzyme using the transformant.

It is another object of the present invention to provide a method for converting reducing amylaceous saccharides with a degree of glucose polymerization of at least 3 into non-reducing saccharides having a trehalose structure as an end unit.

The first object of the present invention is attained by a recombinant thermostable enzyme having the following physicochemical properties:

(1) Action

Forming non-reducing saccharides having a trehalose structure as an end unit from reducing saccharides having a degree of glucose polymerization of at least 3;

(2) Molecular weight

About 69,000–79,000 daltons on sodium dodecylsulfate polyacrylamide gel electrophoresis (SDS-PAGE);

(3) Isoelectric point (pI)

About 5.4–6.4 on isoelectrophoresis; and (4) Thermal stability

Substantially not inactivated even when incubated in an aqueous solution (pH 7.0) at 85° C. for 60 min.

The second object of the present invention is attained by a DNA which encodes the recombinant thermostable enzyme.

The third object of the present invention is attained by a replicable recombinant DNA which contains a self-replicable vector and the recombinant thermostable enzyme.

The fourth object of the present invention is attained by a transformant which is prepared by introducing the replicable recombinant DNA into an appropriate host.

The fifth object of the present invention is attained by a process for preparing the recombinant thermostable enzyme which comprises culturing the transformant in a nutrient culture medium, and collecting the formed recombinant thermostable enzyme from the culture.

The sixth object of the present invention is attained by a method for enzymatically converting reducing amylaceous saccharides which contains a step of allowing the recombinant thermostable enzyme to act on reducing amylaceous saccharides having a degree of glucose polymerization of at least 3 to form non-reducing saccharides having a trehalose structure as an end unit.

BRIEF DESCRIPTION OF THE ACCOMPANYING DRAWINGS

DETAILED DESCRIPTION OF THE INVENTION

Figure 1:
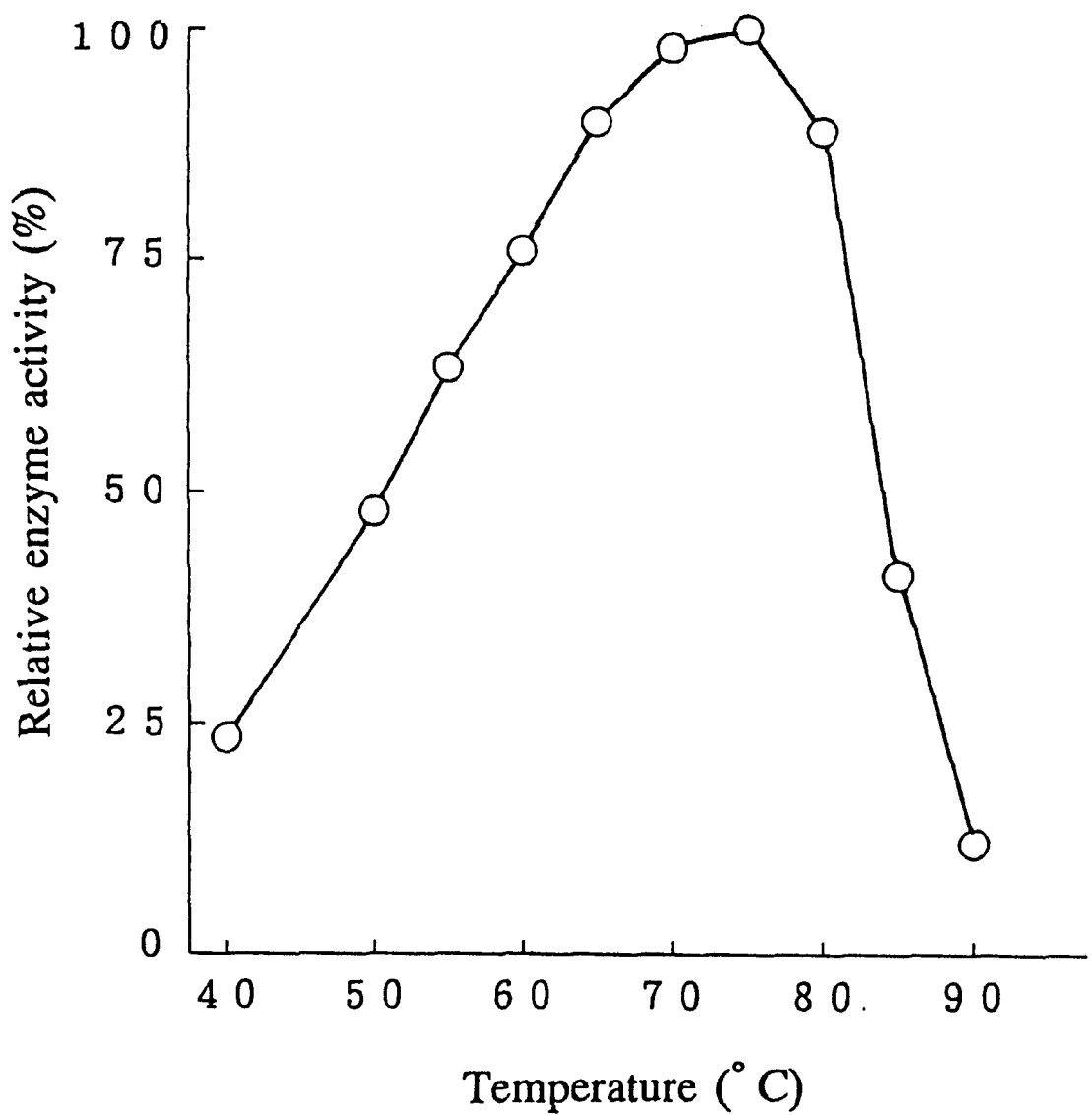
FIG. 1 is a figure of the optimum temperature of a thermostable enzyme produced from *Sulfolobus acidocaldarius* (ATCC 33909).

The recombinant thermostable enzyme according to the present invention forms non-reducing saccharides having a trehalose structure as an end unit from reducing amylaceous saccharides having a degree of glucose polymerization of at least 3 without inactivation even when allow ed to react at a temperature exceeding 55° C.

The DNA according to the present invention expresses the production of the present enzyme by introducing the DNA into an appropriate self-replicable vector to form a replicable recombinant DNA, and introducing the replicable recombinant DNA into an appropriate host which does not produce the present enzyme in itself but readily proliferates.

The recombinant DNA according to the present invention expresses the production of the present enzyme by introducing it into an appropriate host which does not produce the present enzyme but readily proliferates.

The transformant according to the present invention produces the present enzyme when cultured.

Culturing of the transformant by the present process facilitates the production of the present enzyme in a desired amount.

The present conversion method readily converts reducing amylaceous saccharide having a degree of glucose polymerization of at least 3 into non-reducing saccharides having a trehalose structure as an end unit.

The present invention has been accomplished based on the finding of a novel enzyme which forms non-reducing saccharides having a trehalose structure as an end unit from reducing amylaceous saccharides having a degree of glucose polymerization of at least 3. Such an enzyme is obtainable from cultures of microorganisms of the species *Sulfolobus acidocaldarius* (ATCC 33909). The present inventors isolated such an enzyme by using in combination a various purification methods comprising column chromatography as a main technique, studied their properties and features, and revealed that the reality is a polypeptide with the following physicochemical properties:

(1) Action

Forming non-reducing saccharides having a trehalose structure as an end unit from reducing saccharides having a degree of glucose polymerization of at least 3;

(2) Molecular weight

About 69,000–79,000 daltons on sodium dodecyl sulfate polyacrylamide gel electrophoresis (SDS-PAGE);

(3) Isoelectric point (pI)

About 5.4–6.4 on isoelectrophoresis; and (4) Optimum temperature

Exhibiting an optimum temperature of about 75° C. when incubated at a pH 5.5 for 60 min;

(5) Optimum pH

Exhibiting an optimum pH of about 5.0–5.5 when incubated at 60° C. for 60 min;

(6) Thermostability

Stable up to a temperature of about 85° C. even when incubated at a pH 7.0 for 60 min; and (7) pH Stability Stable up to a pH of about 4.0–9.5 when incubated at 4° C. for 24 hours.

The followings are experiments which were conducted to reveal the physicochemical properties of a thermostable enzyme produced from *Sulfolobus acidocaldarius* (ATCC 33909):

Experiment 1

Preparation of Purified enzyme

Into 500-ml flasks were put 100 ml aliquots of a liquid culture medium containing 0.1 w/v % polypeptone, 0.1 w/v % yeast extract, 0.2 w/v % ammonium sulfate, 0.05 w/v % potassium dihydrogen phosphate, 0.02 w/v % magnesium sulfate heptahydrate, 0.02 w/v % potassium chloride, and water, and the flasks were sterilized by autoclaving at 120° C. for 20 min. After cooling the flasks a seed culture of *Sulfolobus acidocaldarius* (ATCC 33909) was inoculated into each liquid culture medium in each flask, followed by the incubation at 75° C. for 24 hours under a rotary shaking condition of 130 rpm to obtain a first seed culture. About 5 L of a fresh preparation of the same liquid culture medium was put in a 10-L fermenter, sterilized similarly as above, cooled to 75° C., and adjusted to a pH 3.0, followed by inoculating one v/v % of the first seed culture into the sterilized liquid culture medium in the fermenter, and culturing the microorganisms at 75° C. for 24 hours under an aeration condition of 500 ml/min. Thereafter, about 250 L of a fresh preparation of the same liquid culture medium was placed in a 300-L fermenter, sterilized similarly as above, cooled to 75° C., and adjusted to a pH 3.0, followed by inoculating one v/v % of the second seed culture into the sterilized liquid culture medium, and culturing the microorganisms at 75° C. for 42 hours under an aeration condition of 100 L/min.

About 170 L of the resultant culture was filtered with an SF membrane, and the filtrate was centrifuged to obtain wet cells. About 258 g of the wet cells was suspended in 300 ml of 10 mM phosphate buffer (pH 7.0) and ultrasonicated to disrupt them. The cell debris thus obtained was centrifuged at 10,000 rpm for 30 min, and about 300 ml of the resultant supernatant was mixed with ammonium sulfate to give a saturation degree of 70 w/v %, allowed to stand at 4° C. for 24 hours, and centrifuged at 10,000 rpm for 30 min. The precipitate was collected, dissolved in an adequate amount of 10 mM Tris-HCl buffer (pH 8.5), and dialyzed against a fresh preparation of the same buffer for 24 hours. Thereafter, the dialyzed solution was centrifuged at 10,000 rpm for 30 min to obtain an about 600 ml of a supernatant with an enzymatic activity.

The supernatant was equally divided into 2 portions which were then respectively fed to a column packed with about 350 ml of "DEAE-TOYOPEARL", a gel for ion-exchange column chromatography commercialized by Tosoh Corporation, Tokyo, Japan, and fed with a linear gradient buffer raging from 0 M to 0.3 M in 10 mM Tris-HCl buffer (pH 8.5). Fractions with an enzymatic activity, eluted at a concentration of about 0.1 M sodium chloride, were collected, pooled, and dialyzed for 10 hours against 10 mM Tris-HCl buffer (pH 8.5) containing one M ammonium sulfate. The dialyzed solution was centrifuged at 10,000 rpm for 30 min to remove insoluble substances, fed to a column packed with about 350 ml of "BUTYL-TOYOPEARL 650", a gel for hydrophobic chromatography commercialized by Tosoh Corporation, Tokyo, Japan, which had been previously equilibrated with 10 mM Tris-HCl buffer (pH 8.5) containing one M ammonium sulfate, and fed with a linear gradient buffer ranging from 1 M to 0 M ammonium sulfate in 10 mM Tris-HCl buffer (pH 8.5).

Fractions with an enzymatic activity eluted at about 0.8 M ammonium sulfate were collected, pooled, dialyzed for 16 hours against 10 mM Tris-HCl buffer (pH 8.5) containing 0.2 M sodium chloride, and centrifuged to remove insoluble substances. The resultant supernatant was fed to a column packed with about 350 ml of "ULTROGEL® AcA", a gel for gel chromatography commercialized by Sepracor, Massachusetts, USA, which had been previously equilibrated with 10 mM Tris-HCl buffer (pH 8.5) containing 0.2 M sodium chloride. Fractions with an enzymatic activity were collected from the eluate, pooled, and dialyzed against 10 mM Tris-HCl buffer (pH 8.5) for 16 hours. The dialyzed solution was centrifuged at 10,000 rpm for 30 min to remove insoluble substances, and the supernatant was fed to a column packed with about 10 ml of "MONO Q", a gel for ion-exchange chromatography commercialized by Pharmacia LKB Uppsala, Sweden, which had been previously equilibrated with 10 mM Tris-HCl buffer (pH 8.5), and eluted with a linear gradient buffer raging from 0 M to 0.2 M sodium chloride in 10 mM Tris-HCl buffer. Fractions with an enzymatic activity eluted at about 0.1 M sodium chloride were collected and pooled for use in the following experiments. The purified enzyme thus obtained had a specific activity of about 81 units/mg protein, and the yield was about 0.24 units per one L of the culture.

When the purified enzyme was in usual manner electrophoresed in 7.5 w/v % polyacrylamide gel, a substantially single band with an enzymatic activity was observed on the gel and revealing that it is extremely high in purity.

Throughout the specification the enzyme activity is expressed by the value measured on the following assay: Place 4 ml of 20 mM acetate buffer (pH 5.5) containing 1.25 w/v % maltopentaose in a test tube, add one ml of an adequately diluted enzyme solution to the test tube, and incubate the mixture solution at 60° C. for 60 min to effect enzymatic reaction. Thereafter, heat the reaction mixture at 100° C. for 30 min to suspend the enzymatic reaction. One ml of the reaction mixture thus obtained is diluted with deionized water by 10 times, and assayed for reducing power on the Somogyi-Nelson's method. As a control, a system using an enzyme solution, which has been heated at 100° C. for 30 min to inactivate the enzyme, is provided and similarly treated as above. One unit activity of the enzyme is defined as the amount of enzyme which reduces the reducing power of one μmol maltopentaose per min under the same conditions as mentioned above.

Experiment 2

Physicochemical property of thermostable enzyme

Experiment 2-1

Action

An aqueous solution containing 10 w/v % of glucose, maltose, maltotriose, maltotetraose, maltopentaose, maltohexaose or maltoheptaose as a substrate was prepared and mixed with 2 units/g substrate, d.s.b., of the purified enzyme in Experiment 1, and the mixture was enzymatically reacted at 60° C. and pH 5.5 for 48 hours. The reaction mixture was desalted in usual manner, and the saccharide composition of the resultant solution was analyzed on high-performance liquid chromatography (HPLC) using a column of "WAKO-BEADS WB-T-330", a column for HPLC commercialized by Wako Pure Chemical Industries, Ltd., Tokyo, Japan. The HPLC procedure was carried out under ambient temperature, and water was used as an eluant and fed to the column at a flow rate of 0.5 ml/min while monitoring the eluate on "MODEL RI-8012", a differential refractometer commercialized by Tosoh Corporation, Tokyo, Japan. The results were in Table 1.

TABLE 1

| Substrate | Saccharide in reaction mixture | Composition (%) |
| --- | --- | --- |
| Glucose | Glucose | 100.0 |
| Maltose | Maltose | 100.0 |
| Maltotriose | Glucose | 9.2 |
|  | Maltose | 18.4 |
|  | Maltotriose | 42.2 |
|  | α-glucosyltrehalose | 30.2 |
| Maltotetraose | Glucose | 6.7 |
|  | Maltose | 2.7 |
|  | Maltotriose | 9.0 |
|  | Maltotetraose | 16.2 |
|  | α-glucosyltrehalose | 8.2 |
|  | α-maltosyltrehalose | 57.2 |
| Maltopentaose | Glucose | 0.7 |
|  | Maltotetraose | 2.0 |
|  | Maltopentaose | 22.9 |
|  | α-maltosyltrehalose | 0.9 |
|  | α-maltotriosyltrehalose | 73.5 |
| Maltohexaose | Glucose | 0.9 |
|  | Maltopentaose | 2.2 |
|  | Maltohexaose | 23.1 |
|  | α-maltotriosyltrehalose | 5.6 |
|  | α-maltotetraosyltrehalose | 68.2 |
| Maltoheptaose | Glucose | 1.0 |
|  | Maltohexaose | 1.4 |
|  | Maltoheptaose | 23.4 |
|  | α-Maltotetraosyltrehalose | 4.2 |
|  | α-Maltopentaosyltrehalose | 70.0 |

The results in Table 1 show that the purified enzyme acted on reducing amylaceous saccharides having a degree of glucose polymerization of at least 3 such as maltotriose, maltotetraose, maltopentaose, maltohexaose and maltoheptaose to form non-reducing saccharides having a trehalose structure as an end unit such as α-glucosyltrehalose, α-maltosyltrehalose, α-maltotriosyltrehalose, α-maltotetraosyltrehalose and α-maltopentaosyltrehalose. In addition to these non-reducing saccharides and intact substrates, glucose and low molecular weight maltooligosaccharides as estimable hydrolysates of the substrates, were detected in the reaction mixtures, and this indicates that the purified enzyme has a hydrolytic activity. The yields of the non-reducing saccharides and hydrolysates from the substrates were respectively 30.2% and 27.6% for maltotriose, 65.4% and 18.4% for maltotetraose, and about 74–75% and about 2–3% for maltopentaose, maltohexaose and maltoheptaose. The purified enzyme formed non-reducing saccharides from maltooligosaccharides having a degree of glucose polymerization of at least 5 in a satisfactory yield, and less hydrolyzed the substrates, but did not newly form any saccharide from glucose and maltose.

Experiment 2-2
Molecular weight

In accordance with the method reported by U. K. Laemmli in *Nature*, Vol.227, pp.680–685 (1970), the purified enzyme in Experiment 1 was electrophoresed on SDS-PAGE to give a single protein band with an enzymatic activity at a position corresponding to about 69,000–79,000 daltons. The marker proteins used in this experiment were myosin (MW=200,000 daltons), β-galactosidase (MW=116, 250 daltons), phosphorylase B (MW=97,400 daltons), serum albumin (MW=66,200 daltons) and ovalbumin (MW=45, 000 daltons).

Experiment 2-3
Isoelectric point

The purified enzyme in Experiment 1 gave an isoelectric point of about 5.4–6.4 on isoelectrophoresis using a polyacrylamide gel containing 2 w/v % ampholine.

Experiment 2-4
Optimum temperature

As is shown in FIG. 1, the optimum temperature of the purified enzyme in Experiment 1 was about 75° C. when incubated in usual manner in 20 mM acetate buffer (pH 5.5) at different temperatures for 60 min.

Experiment 2-5
Optimum pH

Figure 2:
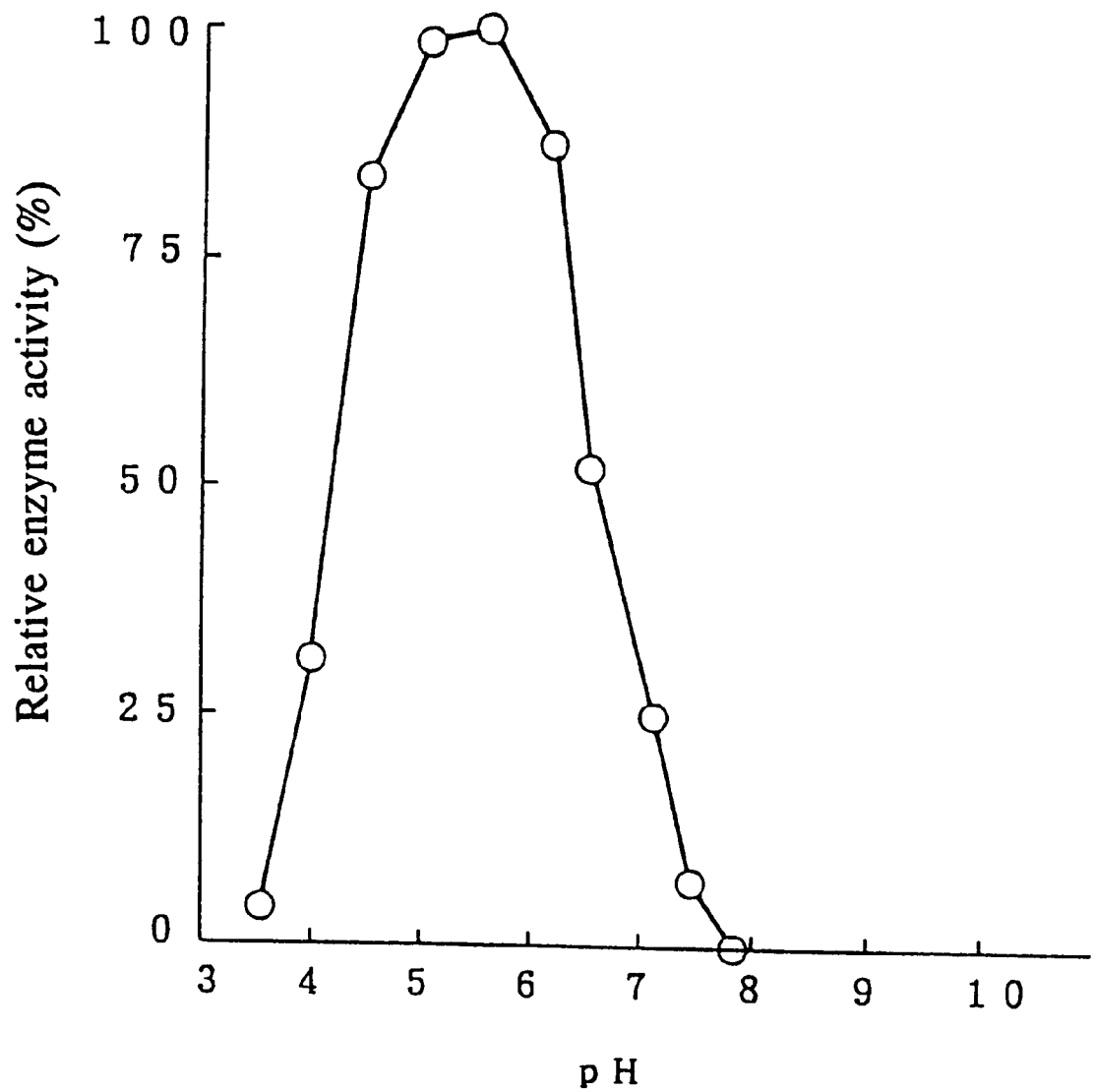
FIG. 2 is a figure of the optimum pH of a thermostable enzyme produced from *Sulfolobus acidocaldarius* (ATCC 33909).

As is shown in FIG. 2, the optimum pH of the purified enzyme in Experiment 1 was about 5.0–5.5 when incubated in usual manner at 60° C. for 60 min in McIlvaine buffer with different pHs.

Experiment 2-6
Thermal stability

Figure 3:
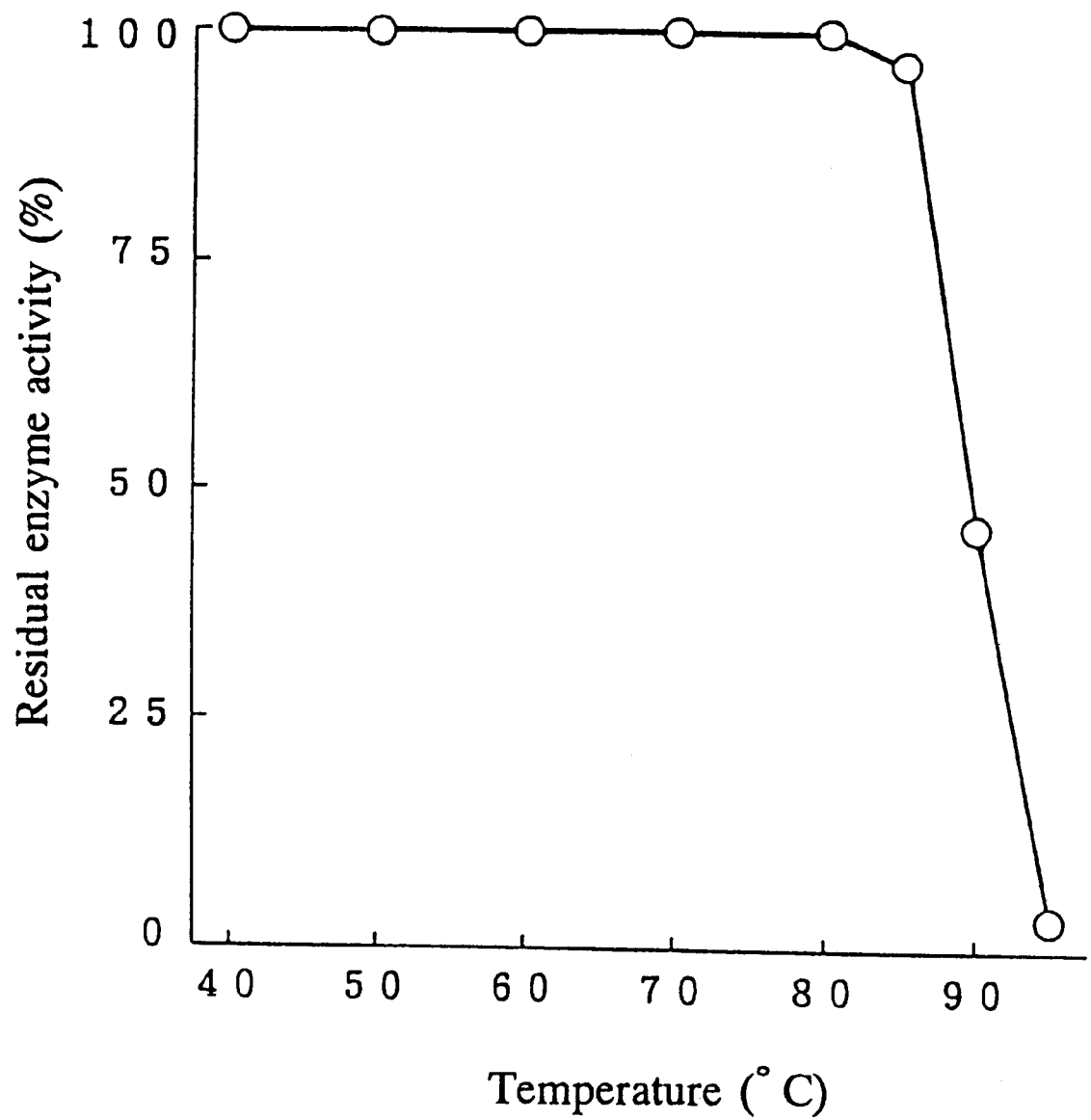
FIG. 3 is a figure of the thermostability of a thermostable enzyme produced from *Sulfolobus acidocaldarius* (ATCC 33909).

As is shown in FIG. 3, the purified enzyme in Experiment 1 was stable up to a temperature of about 85° C. when incubated in usual manner in 10 mM phosphate buffer (pH 7.0) for 60 min.

Experiment 2-7
pH Stability

Figure 4:
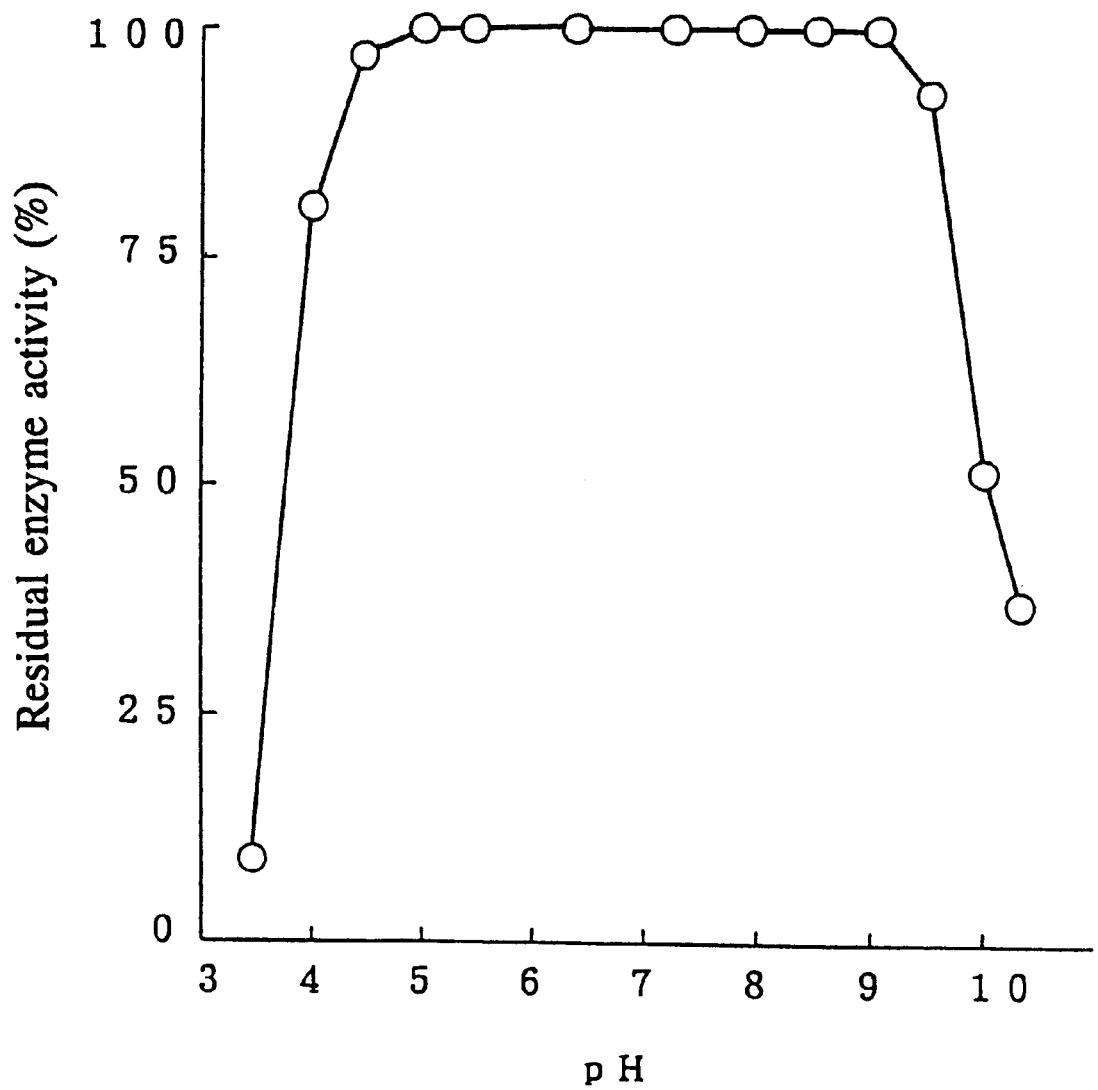
FIG. 4 is a figure of the pH stability of a thermostable enzyme produced from *Sulfolobus acidocaldarius* (ATCC 33909).
Figure 5:
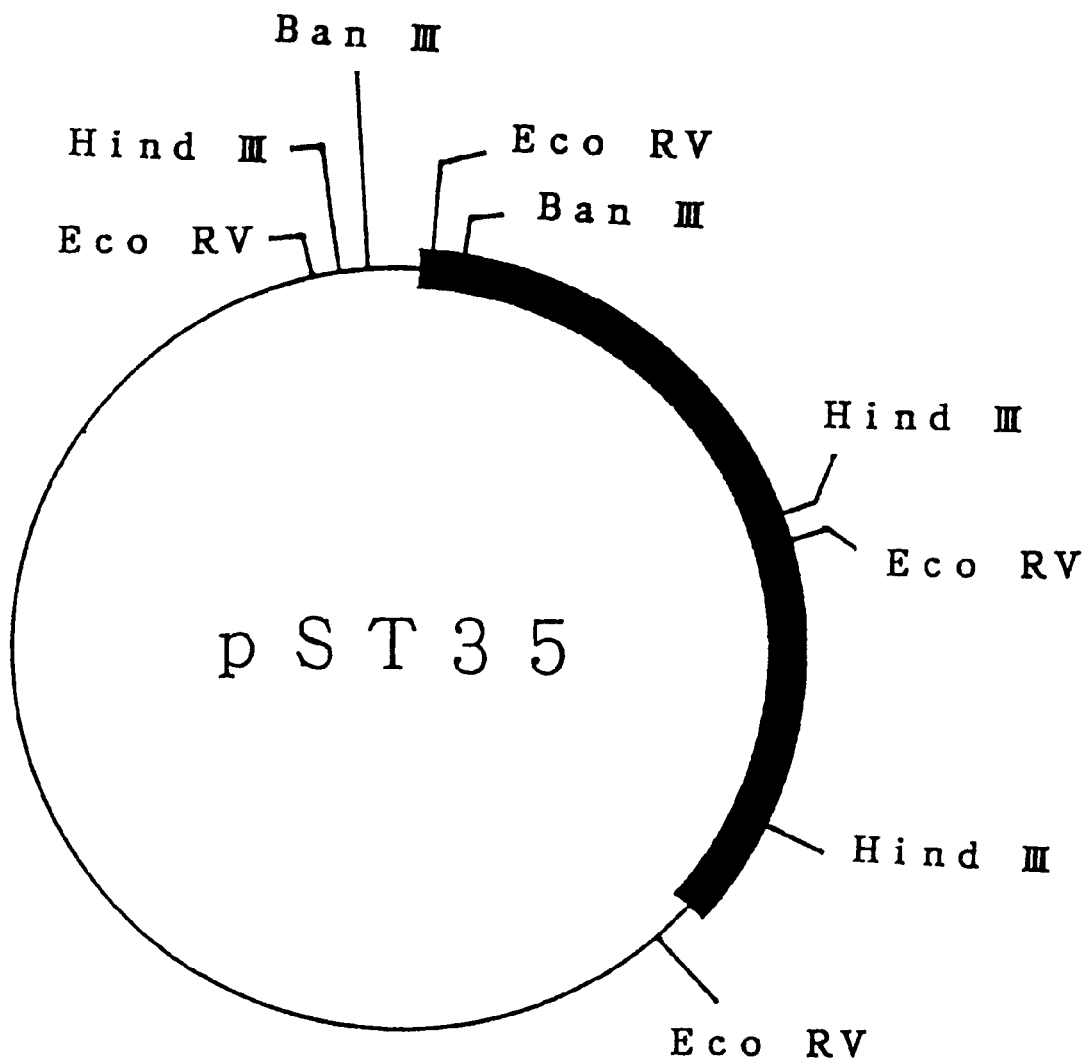
FIG. 5 is a restriction map of the recombinant DNA pST35 according to the present invention.

As is shown in FIG. 4, the purified enzyme in Experiment 1 was stable at a pH in the range of about 4.5–9.5 when incubated in usual manner at 25° C. for 16 hours in McIlvaine buffer or 50 mM sodium carbonate/sodium hydrogen carbonate buffer with different pHs.

Experiment 2-8
Amino acid sequence containing the N-terminal

The amino acid sequence containing the N-terminal of the purified enzyme in Experiment 1 was analyzed on "MODEL 473 A", a gas-phase protein sequencer commercialized by Perkin-Elmer Corp., Instrument Div., Norrwalk, USA, and revealed that it has the amino acid sequence in SEQ ID NO:3.

Experiment 2-9
Partial amino acid sequence

An adequate amount of the purified enzyme in Experiment 1 was weighed, dialyzed against 10 mM Tris-HCl buffer (pH 9.0) at 4° C. for 18 hours, and admixed with 10 mM Tris-HCl buffer (pH 9.0) to give a concentration of about one mg/ml of the enzyme. About one ml of the resultant solution was placed in a container, admixed with 10 μg lysyl endopeptidase, and incubated at 30° C. for 48 hours to partially hydrolyze the enzyme. The resultant hydrolysate was applied to "μBONDAPAK C18", a column for HPLC commercialized by Japan Millipore Ltd., Tokyo, Japan, which had been previously equilibrated with 0.1 v/v % trifluoroacetate containing 16 v/v % aqueous acetonitrile, followed by feeding to the column 0.1 v/v % trifluoroacetate at a flow rate of 0.9 ml/min while increasing the concentration of aqueous acetonitrile from 16 to 48 v/v %, and collecting fractions containing a peptide fragment eluted about 11 min after the initiation of the feeding. The fractions were pooled, dried in vacuo, and dissolved in 0.1 v/v % trifluoroacetate containing 50 v/v % aqueous acetonitrile. Similarly as in Experiment 2-8, the peptide fragment was analyzed and revealed to have an amino acid sequence in SEQ ID NO:4.

Such an enzyme having these physicochemical properties has not been known, and meaning that it is a novel enzyme.

A chromosomal DNA of *Sulfolobus acidocaldarius* (ATCC 33909) was screened by using an oligonucleotide as a probe which had been chemically synthesized based on the partial amino acid sequences in SEQ ID NOs:3 and 4, and this yielded a DNA fragment having a base sequence from the 5'-terminus consisting of about 2,200 base pairs in SEQ ID NO:2. The base sequence of the thermostable enzyme was decoded and revealing that it consists of 720 amino acids and has a partial amino acid sequence from the N-terminal in SEQ ID NO:1.

The sequential experimental steps used to reveal the amino acid sequence and the base sequence in SEQ ID NOs:1 to 2 are summarized in the below:

(1) The thermostable enzyme was isolated from a culture of a donor microorganism, highly purified, and determined for the N-terminal amino acid sequence. The purified enzyme was partially hydrolyzed with protease, and from which a peptide fragment was isolated and determined for amino acid sequence;

(2) A chromosomal DNA was isolated from a donor microorganism, purified and partially digested with a restriction enzyme to obtain a DNA fragment consisting of about 2,000–6,000 base pairs. The DNA fragment was ligated by DNA ligase to a plasmid vector, which had been previously cleaved with a restriction enzyme, to obtain a recombinant DNA;

(3) The recombinant DNA thus obtained was introduced into *Escherichia coli* to obtain transformants, and from which an objective transformant containing a DNA which encodes the objective enzyme was selected by the colony hybridization method using as a probe an oligonucleotide which had been chemically synthesized based on the above partial amino acid sequence; and (4) The recombinant DNA was obtained from the transformant and annealed with a primer, followed by allowing a DNA polymerase to act on the resultant to extend the primer, and determining the base sequence of the resultant complementary chain DNA by the dideoxy chain termination method. The comparison of an amino acid sequence, that could be estimated from the base sequence, with the aforesaid amino acid sequence confirmed that the base sequence encodes the enzyme.

The following Experiments 3 and 4 will concretely explain the above steps (2) to (4), and the techniques in themselves used therein are well known in this art, for example, those described by J. Sumbruck et al. in *"Molecular Cloning A Laboratory Manual"*, 2nd edition, published by Cold Spring Harbor Laboratory Press, USA (1989).

Experiment 3
Preparation of recombinant DNA containing DNA which encodes thermostable enzyme, and transformant obtained therewith Experiment 3-1
Preparation of chromosomal DNA To 500-ml flasks were placed about 100 ml aliquots of a liquid culture medium consisting of 0.1 w/v % polypeptone, 0.1 w/v % yeast extract, 0.2 w/v % ammonium sulfate, 0.05 w/v % potassium dihydrogen phosphate, 0.02 w/v % magnesium sulfate heptahydrate, 0.02 w/v % potassium chloride, and water, and the flasks were sterilized by autoclaving at 120° C. for 20 min, cooled, and adjusted to a pH 3.0 by the addition of sulfate. A seed culture of *Sulfolobus acidocaldarius* (ATCC 33909) was inoculated into each flask, incubated at 75° C. for 24 hours under a rotary shaking condition of 130 rpm to obtain a seed culture. About 5 L of a fresh preparation of the same liquid nutrient culture medium was placed in a 10-L fermenter, sterilized similarly as above, cooled to 75° C., adjusted to a pH 3.0, and inoculated with one v/v % of the seed culture, followed by the incubation at 75° C. for 24 hours under an aeration condition of 500 ml/min.

The resultant cells were collected by centrifugation, suspended in TES buffer (pH 8.0), admixed with 0.05 w/v % lysozyme, and incubated at 37° C. for 30 min. The resultant was freezed at −80° C. for one hour, admixed with TES buffer (pH 9.0), heated to 60° C., and admixed with a mixture solution of TES buffer and phenol, and the resultant mixture was chilled with ice and centrifuged to obtain a supernatant. To the supernatant was added 2 fold volumes of cold ethanol to precipitate a crude chromosomal DNA which was then collected, dissolved in SSC buffer (pH 7.1), admixed with 7.5 μg ribonuclease and 125 μg protease, and incubated at 37° C. for one hour. Thereafter, a mixture solution of chloroform and isoamyl alcohol was added to the reaction mixture to extract the objective chromosomal DNA. The resultant solution was admixed with cold ethanol, followed by collecting the formed sediment containing the chromosomal DNA. The purified chromosomal DNA thus obtained was dissolved in SSC buffer (pH 7.1) to give a concentration of about one mg/ml, and the solution was freezed at −80° C.

Experiment 3-2
Preparation of recombinant DNA pST35 and transformant ST35

One ml of the purified chromosomal DNA in Experiment 3-1 was placed in a container, admixed with about 35 units of Sau 3AI, a restriction enzyme, and enzymatically reacted at 37° C. for 20 min to partially digest the chromosomal DNA, followed by recovering a DNA fragment consisting of about 2,000–6,000 base pairs by sucrose density-gradient ultracentrifugation. One μg of Bluescript II SK(+), a plasmid vector, was weighed, subjected to the action of Bam HI, a restriction enzyme, to completely digest the plasmid vector, and admixed with 10 μg of the DNA fragment and 2 units of T4 DNA ligase. The mixture was allowed to stand at 4° C. overnight to ligate the DNA fragment to the plasmid vector.

To the resultant recombinant DNA was added 30 μl of "Epicurian Coli® XLI-Blue", a competent cell commercialized by Toyobo Co., Ltd., Tokyo, Japan, allowed to stand under ice-chilling conditions for 30 min, heated to 42° C., admixed with SOC broth, and incubated at 37° C. for one hour to introduce the recombinant DNA into *Escherichia coli*.

The transformant thus obtained was inoculated into agar plate (pH 7.0) containing 50 μg/ml of 5-bromo-4-chloro-3-indolyl-β-galactoside, and cultured at 37° C. for 18 hours, followed by placing a nylon film on the agar plate to fix thereon about 5,000 colonies formed on the agar plate. Based on the amino acid sequence Asn-Leu-Trp-Tyr-Phe-Lys-Asp, probe 1 represented by the base sequence of 5'-AAYYTNTGGTAYTTYAARGA-3' was chemically synthesized, labelled with $^{32}$P, and hybridized with the colonies of transformants fixed on the nylon film, followed by selecting 15 transformants which exhibited a strong hybridization.

The objective recombinant DNA was selected in usual manner from the 15 transformants, and, in accordance with the method described by E. M. Southern in *Journal of Molecular Biology*, Vol.98, pp.503–517 (1975), hybridized with prove 2 having the base sequence of 5'-GARGARTGGCAYWSNATHAT-3'(SEQ ID NO:8) which had been chemically synthesized based on the amino acid sequence of Glu-Glu-Trp-His-Ser-Ile-Ile (amino acids 2–8 of SEQ ID NO:4) and labelled with $^{32}$P, followed by selecting a recombinant DNA which exhibited a strong hybridization. The recombinant DNA and transformant were respectively named "pST35" and "ST35".

The transformant ST35 was inoculated into L-broth (pH 7.0) containing 100 μg/ml ampicillin, and cultured at 37° C. for 24 hours with a rotary shaker. After completion of the culture, the cells were collected from the culture by centrifugation, and treated with the alkaline method in general to extracellularly extract the recombinant DNA. The resultant extract was in usual manner purified and analyzed to find that the recombinant DNA pST35 consists of about 6,200 base pairs and has a DNA, which encodes the enzyme and consists of about 2,200 base pairs, in the downstream of the cleave site of Eco RV, a restriction enzyme.

Experiment 3-3
Production of recombinant thermostable enzyme by transformant ST35

To 500-ml flasks were added about 100 ml aliquots of a liquid culture medium (pH 7.0) consisting of 0.1 w/v % polypeptone, 0.1 w/v % yeast extract, 0.2 w/v % ammonium sulfate, 0.05 w/v % potassium dihydrogen phosphate, 0.02 w/v % magnesium sulfate heptahydrate, 0.02 w/v % potassium chloride, and water. The flasks were sterilized by autoclaving at 120° C. for 20 min, cooled, admixed with 50 μg/ml ampicillin, and inoculated with a seed culture of transformant ST35 in Experiment 3-2, followed by culturing the transformant at 37° C. for 24 hours under a rotary shaking condition of 130 rpm to obtain a seed culture. About 5 L of a fresh preparation of the same liquid culture medium was placed in a 10-L fermenter, sterilized similarly as above, cooled to 37° C., admixed with 50 μg/ml ampicillin, inoculated with one v/v % of the seed culture, followed by the incubation at 37° C. for 24 hours under an aeration condition of 500 ml/min.

The resultant culture was in usual manner treated with ultrasonic to disrupt cells, and the resultant suspension was centrifuged to remove insoluble substances. The supernatant thus obtained was admixed with ammonium sulfate to give a saturation degree of 70 w/v %, allowed to stand at 4° C.

for 24 hours, and centrifuged to obtain a precipitate which was then dissolved in a small amount of 10 mM phosphate buffer (pH 8.5). The resultant solution was dialyzed against a fresh preparation of the same buffer for 10 hours, and the dialyzed solution was assayed for enzymatic activity and revealing that one L of the culture yielded about 8.0 units of the recombinant thermostable enzyme.

As a control, a seed culture of *Escherichia coil* XLI-Blue strain or *Sulfolobus acidocaldarius* (ATCC 33909) was inoculated into a fresh preparation of the same liquid culture medium but free of ampicillin. In the case of culturing *Sulfolobus acidocaldarius* (ATCC 33909), it was cultured and treated similarly as above except that the initial pH of the nutrient culture medium and the culturing temperature were respectively set to 3.0 and 75° C. Assaying the resultant enzymatic activity, one L culture of *Sulfolobus acidocaldarius* (ATCC 33909) yielded about 1.8 units of the thermostable enzyme, and the yield was significantly lower than that of transformant ST35. *Escherichia coli* XLI-Blue strain used as a host did not form the thermostable enzyme.

Thereafter, the recombinant thermostable enzyme produced by the transformant ST35 was purified similarly as in Experiments 1 and 2 and examined for properties and features and revealing that it has substantially the same physicochemical properties of the thermostable enzyme from *Sulfolobus acidocaldarius* (ATCC 33909) because (i) the recombinant thermostable enzyme has a molecular weight of about 69,000–79,000 daltons on SDS-PAGE and an isoelectric point of about 5.4–6.4 on isoelectrophoresis, and (ii) it is not substantially inactivated even when incubated in an aqueous solution (pH 7.0) at 85° C. for 60 min. These results indicate that the present thermostable enzyme can be prepared by the recombinant DNA technology with a significantly improved yield.

Experiment 4
Preparation of complementary DNA, and determination of base sequence and amino acid sequence Two μg of the recombinant DNA pST35 in Experiment 3-2 was weighed, degenerated by the addition of 2 M aqueous sodium hydroxide solution, and admixed with an adequate amount of cold ethanol, followed by collecting the resultant sediment containing a template DNA and drying the sediment in vacuo. To the template DNA were added 50 pmole/ml of a chemically synthesized primer having the base sequence of 5'-GTAAAACGACG GCCAGT-3'(SEQ ID NO:19) and 10 μl of 40 mM Tris-HCl buffer (pH 7.5) containing 20 mM magnesium chloride and sodium chloride, and the mixture was incubated at 65° C. for 2 min to effect annealing. The resultant mixture was admixed with 2 μl of an aqueous solution containing 7.5 μM dATP, dGTP and dTTP respectively, 0.5 μl of [α-$^{32}$P]dCTP (2 mCi/ml), one μl of 0.1 M dithiothreitol, and 2 μl of 1.5 units/ml T7 DNA polymerase, followed by the incubation at 25° C. for 5 min to extend the primer from the 5'-terminus to the 3'-terminus. Thus, a complementary chain DNA was obtained.

The reaction product containing the complementary chain DNA was divided into quarters, to each of which 2.5 μl of 50 mM aqueous sodium chloride solution containing 80 μM dNTP and 8 μM ddATP, ddCTP, ddGTP or ddTTP was added, and the resultant mixture was incubated at 37° C. for 5 min, followed by suspending the reaction by the addition of 4 μl of 98 v/v % aqueous formamide solution containing 20 mM EDTA, 0.05 w/v % bromophenol blue and 0.05 w/v % xylene cyanol. The reaction mixture was placed in a container, heated in a boiling-water bath for 3 min, placed on a gel containing 6 w/v % polyacrylamide, and electrophoresed by energizing the gel with a constant voltage of about 2,000 volts to separate DNA fragments, followed by fixing the gel in usual manner, drying it and subjecting the resultant to autoradiography.

Analyses of the DNA fragments separated on the radiogram revealed that the complementary chain DNA contains the base sequence consisting of 2,200 base pairs in SEQ ID NO:5. An amino acid sequence that could be estimated from the base sequence was in SEQ ID NO:5, and it was compared with the partial amino acid sequences in SEQ ID NOs:3 and 4, and revealing that the partial amino acid sequence in SEQ ID NO:3 corresponded to that positioning from 1 to 30 in SEQ ID NO:5, and that in SEQ ID NO:4 corresponded to that positioning from 468 to 478 in SEQ ID NO:5. These results indicate that the present recombinant thermostable enzyme has the amino acid sequence from the N-terminal in SEQ ID NO:1, and, in the case of the DNA derived from *Sulfolobus acidocaldarius* (ATCC 33909), the amino acid sequence is encoded by the base sequence from the 5'-terminus in SEQ ID NO:2.

As is explained in the above, the thermostable enzyme, which forms non-reducing saccharides having a trehalose structure as an end unit from reducing amylaceous saccharides having a degree of glucose polymerization of at least 3, was found as a result of the present inventors' long-term research. The thermostable enzyme has distinct physicochemical properties from those of other conventional enzymes. The present invention is to produce the thermostable enzyme by using the recombinant DNA technology. The present recombinant thermostable enzyme, as well as its preparation and uses, will be explained in detail with reference to the later described Examples.

The recombinant thermostable enzyme as referred to in the present invention means thermostable enzymes in general which are preparable by the recombinant DNA technology and capable of forming non-reducing saccharides having a trehalose structure as an end unit from reducing amylaceous saccharides having a degree of glucose polymerization of at least 3. Generally, the recombinant thermostable enzyme according to the present invention has a revealed amino acid sequence, and, as an example, the amino acid sequence from the N-terminal as shown in SEQ ID NO: 1, and homologous ones to it can be mentioned. Variants having amino acid sequences homologous to the one in SEQ ID NO:1 can be obtained by replacing one or more amino acids in SEQ ID NO:1 with other amino acids without substantially alternating the inherent physicochemical properties. Although even when used the same DNA and it also depends on hosts into which the DNA is introduced, the ingredients and components of nutrient culture media for culturing transformants, and their cultivation temperature and pH, there may be produced modified enzymes which have the inherent physicochemical properties but defect one or more amino acids in SEQ ID NO:1, or those which have one or more amino acids added newly to the N-terminal after the DNA expression as the result of the modification of intracellular enzymes of the hosts. Such variants can be used in the present invention as long as they have the desired physicochemical properties.

The recombinant thermostable enzyme can be obtained from cultures of transformants containing a specific DNA. Examples of such transformants usable in the present invention can be prepared by introducing into hosts a DNA which has either the base sequence from the 5'-terminus in SEQ ID NO:2 or a homologous base sequence to it or a complementary base sequence to them. These base sequences may be modified by replacing one or more bases of them without alternating the amino acid sequences encoded by them by means of the degeneracy of genetic code. Needless to say, one or more bases in such base sequences which encode the recombinant thermostable enzyme or their variants can be readily replaced with other bases to allow the DNA to express the objective thermostable enzyme production in hosts.

The DNA usable in the present invention includes those are derived from natural resources and those which are artificially synthesized as long as they have the aforesaid base sequences. The natural resources for the DNA according to the present invention are, for example, microorganisms of the genus Sulfolobus such as *Sulfolobus acidocaldarius* (ATCC 33909), and from which genes containing the present DNA can be obtained. The aforementioned microorganisms can be inoculated in nutrient culture media and cultured for about 1–3 days under aerobic conditions, and the resultant cells were collected from the cultures and subjected to ultrasonication or treated with a cell-wall lysis enzyme such as lysozyme or β-glucanase to extract genes containing the present DNA. In this case, a proteolytic enzyme such as protease can be used along with the cell-wall lysis enzyme, and, when treated the cells with an ultrasonic disintegrator, they may be treated in the presence of a surfactant such as sodium dodecyl sulfate (SDS) or with freezing and thawing method. The objective DNA is obtainable by treating the resultant with phenol extraction, alcohol sedimentation, centrifugation, protease treatment and/or ribonuclease treatment generally used in this field. To artificially synthesize the present DNA, it can be chemically synthesized by using the base sequence in SEQ ID NO:2, or can be obtained in a plasmid form by inserting a DNA, which encodes the amino acid sequence in SEQ ID NO:1, into an appropriate self-replicable vector to obtain a recombinant DNA, introducing the recombinant DNA into an appropriate host to obtain a transformant, culturing the transformant, separating the proliferated cells from the resultant culture, and collecting plasmids containing the objective DNA from the cells.

Such a DNA is generally introduced into hosts in a recombinant DNA form. Generally, the recombinant DNA contains the aforesaid DNA and a self-replicable vector, and it can be prepared with a relative easiness by the recombinant DNA technology in general when the material DNA is in hand. Examples of such a vector are plasmid vectors such as pBR322, pUC18, Bluescript II SK(+), pKK223-3, pUB110, pTZ4, pC194, pHV14, TRp7, TEp7, pBS7, etc.; and phage vectors such as λgt•λC, λgt•λB, ρ11, φ1, φ105, etc. Among these plasmid- and phage-vectors, pBR322, pUC18, Bluescript II SK(+), pKK223-3, λgt•λC and λgt•λB are satisfactorily used when the present DNA should be expressed in *Escherichia coli*, while pUB110, pTZ4, pC194, ρ11, φ1 and φ105 are satisfactorily used to express the DNA in microorganisms of the genus Bacillus. The plasmid vectors pHV14, TRp7, TEp7 and pBS7 are advantageously used when the recombinant DNA is allowed to grow in 2 or more hosts.

The methods used to insert the present DNA into such vectors in the present invention may be conventional ones in generally used in this field. A gene containing the present DNA and a self-replicable vector are first digested with a restriction enzyme and/or ultrasonic, then the resultant DNA fragments and vector fragments are ligated. To digest DNAs and vectors, restriction enzymes which specifically act on nucleotides, particularly, type II restriction enzymes, more particularly Sau 3AI, Eco RI, Hind III, Bam HI, Sal I, Xba I, Sac I, Pst I, Ban III, Spe I, etc., facilitate the ligation of the DNA fragments and vector fragments. To ligate the DNA fragments with the vector fragments, they are, if necessary, annealed and subjected to the action of a DNA ligase in vivo or in vitro. The recombinant DNA thus obtained is replicable without substantial limitation by introducing it into appropriate hosts, and culturing the resultant transformants.

The recombinant DNA thus obtained can be introduced into appropriate host microorganisms including *Escherichia coli* and those of the genus Bacillus as well as actinomyces and yeasts. In the case of using *Escherichia coli* as a host, the DNA can be introduced thereinto by culturing the host in the presence of the recombinant DNA and calcium ion, while in the case of using a microorganism of the genus Bacillus as a host the competent cell method and the colony hybridization method can be used. Desired transformants can be cloned by the colony hybridization method or by culturing a variety of transformants in nutrient culture media containing reducing amylaceous saccharides having a degree of glucose polymerization of at least 3, and selecting the objective transformants which form non-reducing saccharides having a trehalose structure as an end unit from the reducing amylaceous saccharides.

The transformants thus obtained intra- and extracellularly produce the objective enzyme when cultured in nutrient culture media. Generally, liquid culture media in general supplemented with carbon sources, nitrogen sources and minerals, and, if necessary, further supplemented with small amounts of amino acids and vitamins can be used in the invention. Examples of the carbon sources are saccharides such as unprocessed starch, starch hydrolysate, glucose, fructose, sucrose and trehalose. Examples of the nitrogen sources are organic- and inorganic-substances containing nitrogen such as ammonia and salts thereof, urea, nitrate, peptone, yeast extract, defatted soy been, corn steep liquor, and beef extract. Cultures containing the objective enzyme can be prepared by inoculating the transformants into nutrient culture media, and incubating them at a temperature of 20–65° C. and a pH of 2–9 for about 1–6 days under aerobic conditions by the aeration-agitation method. Such cultures can be used intact as a crude enzyme, and, usually, cells in the cultures may be disrupted prior to use with ultrasonic and/or cell-wall lysis enzymes, followed by separating the thermostable enzyme from intact cells and cell debris by filtration and/or centrifugation and purifying the enzyme. The methods to purify the enzyme include conventional ones in general. From cultures intact cells and cell debris are eliminated and subjected to one or more methods such as concentration, salting out, dialysis, separatory sedimentation, gel filtration chromatography, ion-exchange chromatography, hydrophobic chromatography, affinity chromatography, gel electrophoresis and isoelectric point electrophoresis.

As is described above, the recombinant thermostable enzyme according to the present invention has a specific feature of forming non-reducing saccharides having a trehalose structure as an end unit from reducing amylaceous saccharides having a degree of glucose polymerization of at least 3 even when allowed to act on at a temperature exceeding 55 C. The formed non-reducing saccharides have a satisfactorily mild and high-quality sweetness as well as an adequate viscosity and moisture-retaining ability, and, as a great advantageous feature, they can sweeten food products without fear of causing unsatisfactory coloration and deterioration because they have no reducing residue within their molecules. With these features a variety of amylaceous saccharides, which have been put aside because of their reducibilities, can be converted into saccharides which have a satisfactory handleability, usefulness, and no substantial reducibility or extremely-reduced reducibility.

Explaining now the conversion method in more detail, reducing starch hydrolysates, which are obtainable by partially hydrolyzing amylaceous saccharides such as starch, amylopectin and amylose with acids and/or amylases, can be usually used as the substrate for the present recombinant thermostable enzyme. Such reducing starch hydrolysate can be obtained by conventional methods generally used in this field, and examples of such include one or more maltooligosaccharides having a degree of glucose polymerization of at least 3, for example, maltotriose, maltotetraose, maltopentaose, maltohexaose and maltoheptaose. As is described in "Handbook of Amylases and Related Enzymes", 1st edition (1988), edited by The Amylase Research Society of Japan, published by Pergamon Press plc, Oxford, England, α-amylase, maltotetraose-forming amylase, maltopentaose-forming amylase and maltohexaose-forming amylase are especially useful to prepare the reducing amylaceous saccharides used in the present invention, and, the use of any one of these amylases facilitates the production of mixtures of amylaceous saccharides rich in reducing amylaceous saccharides having a degree of glucose polymerization of at least 3 in a considerably-high yield. If necessary, the combination use of the amylases and starch debranching enzymes such as pullulanase and isoamylase can increase the yield of the reducing amylaceous saccharides used as the substrate for the present recombinant thermostable enzyme.

In the enzymatic conversion method according to the present invention, the present recombinant thermostable enzyme is generally allowed to coexist in an aqueous solution containing one or more of the above reducing amylaceous saccharides as a substrate, followed by the enzymatic reaction at a prescribed temperature and pH until a desired amount of the objective reducing amylaceous saccharides is formed. Although the enzymatic reaction proceeds even below a concentration of 0.1 w/w %, d.s.b., of a substrate, a concentration of 2 w/w % or higher, d.s.b., preferably, in the range of 5–50 w/w %, d.s.b., of a substrate can be satisfactorily used when used the present conversion method in an industrial-scale production. The temperature and pH used in the enzymatic reaction are set to within the range of which does not inactivate the recombinant thermostable enzyme and allows the enzyme to effectively act on substrates, i.e. a temperature of higher than 55° C. but not higher than 85° C., preferably, a temperature in the range of about 56–70° C., and a pH of 4–7, preferably, a pH in the range of about 5–6. The amount and reaction time suitable for the present recombinant thermostable enzyme are chosen depending on the enzymatic reaction condition. Thus, the present recombinant thermostable enzyme converts reducing amylaceous saccharides having a degree of glucose polymerization of at least 3 into non-reducing saccharides having a trehalose structure as an end unit, e.g. the conversion rate reaches up to about 74% when acts on maltopentaose.

The reaction mixtures obtained by the present conversion reaction can be used intact, and, usually, they are purified prior to use: Insoluble substances are eliminated from the reaction mixtures by filtration and centrifugation, and the resultant solutions are decolored with activated charcoals, desalted and purified on ion exchangers, and concentrated into syrupy products. Depending on their use, the syrupy products are dried in vacuo and spray-dried into solid products. In order to obtain products which substantially consist of non-reducing saccharides, the aforesaid syrupy products are subjected to one or more methods such as chromatography using an ion exchanger, activated charcoal and silica gel for saccharide separation, separatory sedimentation using alcohol and/or acetone, membrane filtration, fermentation by yeasts, and removal and decomposition of reducing saccharides by alkalis. The methods to treat a relatively-large amount of reaction mixture are, for example, fixed bed- or pseudomoving bed-ion exchange chromatography as disclosed in Japanese Patent Laid-Open Nos.23, 799/83 and 72,598/83, and such a method produces non-reducing saccharide-rich products on an industrial scale and in a considerably-high yield.

The non-reducing saccharides thus obtained have a wide applicability to a variety of products which are apt to be readily damaged by the reducibility of saccharide sweeteners: For example, they can be satisfactorily used in food products, cosmetics and pharmaceuticals as a sweetener, taste-improving agent, quality-improving agent, stabilizer, filler, excipient and adjuvant. Since the non-reducing saccharides almost qualitatively form trehalose when received an enzymatic action of a trehalose-releasing enzyme as disclosed in Japanese Patent Application No.79,291/94, they can be used as an intermediate for producing trehalose which could not have been readily prepared.

The following Examples explain in detail the preparation of the present recombinant thermostable enzyme, and the enzymatic conversion method of reducing amylaceous saccharides using the enzyme:

EXAMPLE A-1

Preparation of recombinant thermostable enzyme

In 500-ml flasks were placed 100 ml aliquots of a liquid culture medium (pH 7.0) consisting of one w/v % polypeptone, 0.5 w/v % yeast extract, 0.5 w/v % sodium chloride, and water, and to each flask was sterilized by autoclaving at 120° C. for 20 min, and admixed with 50 μg/ml ampicillin. Thereafter, the flasks were cooled and inoculated with the transformant ST35 obtained by the method in Experiment 3-2, followed by the culture of the transformant at 37° C. for 24 hours under a rotary shaking condition of 130 rpm to obtain a seed culture. To 30-L fermenter was placed about 18 L of a fresh preparation of the same liquid culture medium, sterilized similarly as above, cooled to 37° C., admixed with 50 μg/ml ampicillin, and inoculated with one v/v % of the seed culture, followed by the culture at 37° C. for 24 hours under aeration and agitation conditions.

The resultant culture was treated with ultrasonic to disrupt cells, and the resultant suspension was centrifuged to remove insoluble substances, followed by assaying the enzymatic activity in the supernatant to find that one L of the culture contained about 75 units of the present recombinant thermostable enzyme. The culture supernatant was purified by the method in Experiment 1 to obtain an about 10 ml aqueous solution containing about 57 units/ml of the present recombinant thermostable enzyme having a specific activity of about 80 units/mg protein.

EXAMPLE A-2

Preparation of recombinant thermostable enzyme

EXAMPLE A-2 (a)

Preparation of transformant

Ten oligonucleotides, which were chemically synthesized by conventional method and had the following base sequences represented by 5'-GATCCGTTCTGGCAAATATTCTGAAATGAGCTGT-3', 5'(SEQ ID NO:9)-

TGACAATTAATCATCGGCTCGTCTAATGTGTGGAAT TCTGATTCGA-3'(SEQ ID NO:10), 5'-ATTTTTTAATAAAATCAGGAGGAAAAAATATGAT ATCAGCAACCTACA-3'(SEQ ID NO:11), 5'-GATTACAGTTAAATAAGAATTTTAATTTTGGTGA CGTAATCGATGAA-3'(SEQ ID NO:12), 5'-TTCACTAGTTAGAATGTGATGAAGGCCTGCGGCC GCTGCAGAGCTCA-3'(SEQ ID NO:13), 5'-CGATGATTAATTGTCAACAGCTCATTTCAGAATAT TTGCCAGAAGC-3'(SEQ ID NO:14), 5'-TTTTATTAAAAAATTCGAATCAGAATTCCACACAT TAGACGAGC-3'(SEQ ID NO:15), 5'-TTAACTGTAATCTGTAGGTTGCTGATATCATATTTT TTCCTCCTGA-3'(SEQ ID NO:16), 5'-TAGTGAATTCTACGATTACGTCACCAAAATTAAA ATTCTTAT-3'(SEQ ID NO:17), and 5'-AGCTTGAGCTCTGCAGCGGCCGCAGGCCTTCAT ACATTCTAAC-3'(SEQ ID NO:18), were mixed in an appropriate ratio, and the mixture was successively incubated at 100° C., 65° C., 37° C. and 20° C. for each 20 min to anneal them. The resultant double strand DNA having the base sequence in SEQ ID NO:6 was admixed with "pKK223-3", a plasmid vector commercialized by Pharmacia LKB Biotechnology AB, Uppsala, Sweden, which had been cleaved with restriction enzymes Bam HI and Hind III, and the mixture was allowed to stand at 4° C. overnight in the presence of T4 DNA ligase to effect ligation and resulting in the formation of a first recombinant DNA having the base sequences of bases 1 through 59 and those 2,149 through 2,160 of SEQ ID NO:2. The first recombinant DNA corresponded to the base sequence in SEQ ID NO:2 wherein the first base "G (guanine)" was replaced with "A (adenine)".

A recombinant DNA pST35 obtained by the method in Experiment 3-2 was cleaved with recombinant enzymes Ban III and Spe I to obtain a DNA fragment consisting of about 2,090 base pairs having a base sequence of bases 60 through 2,148 of SEQ ID NO:2. Similarly as in the above, the DNA fragment was ligated to the first recombinant DNA which had been cleaved with restriction enzymes Ban III and Spe I to obtain the present recombinant DNA pST36 having 2,160 base pairs corresponding to the base sequence of SEQ ID NO:2 wherein the first base "G (guanine)" was replaced with "A (adenine)" without alternating the amino acid sequence of SEQ ID NO:1.

Figure 6:
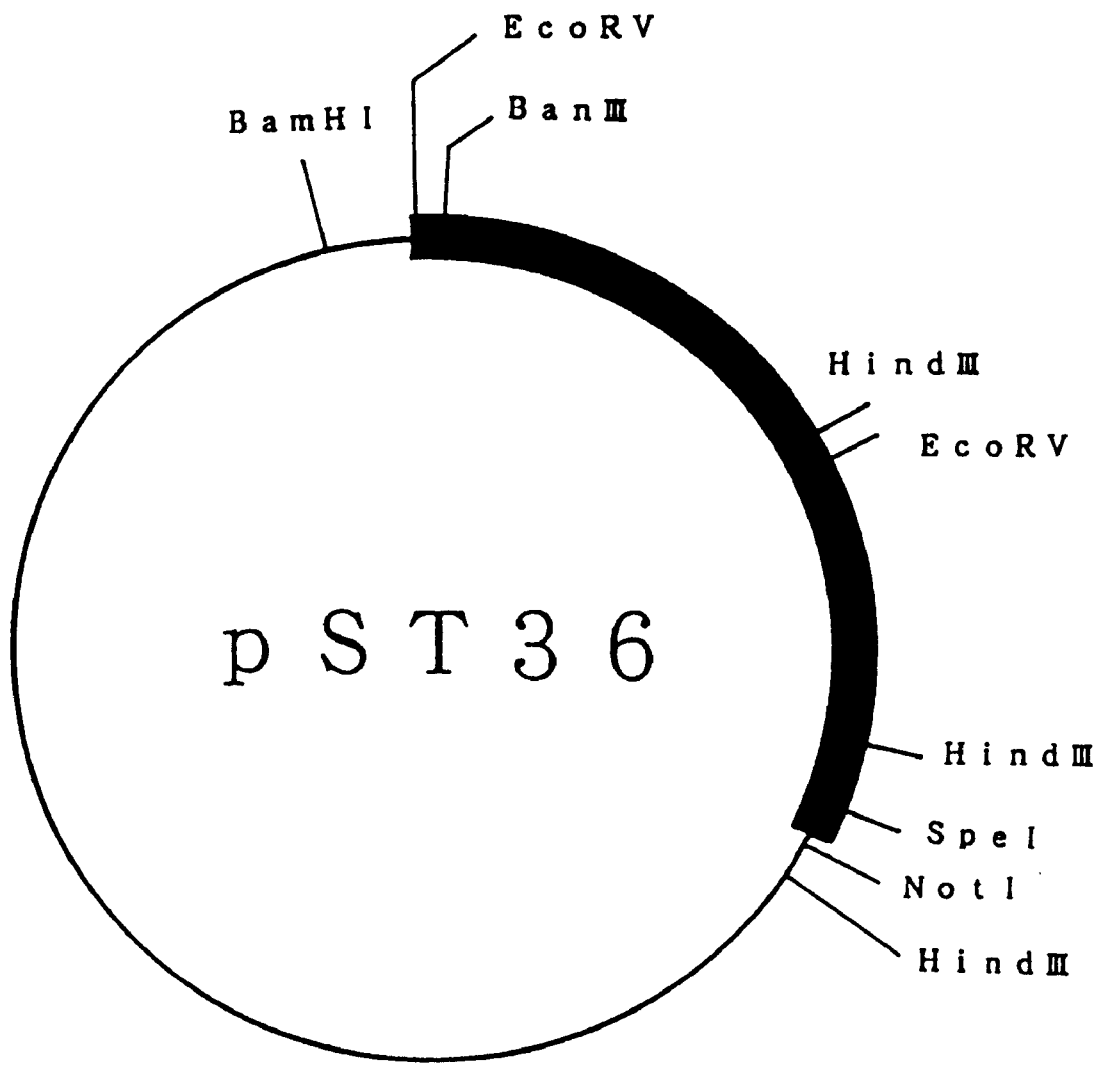
FIG. 6 is a restriction map of the recombinant DNA pST36 according to the present invention.

In accordance with the method in Experiment 3-2, the recombinant DNA pST36 was introduced into "BMH71-18", a competent cell commercialized by Takara Shuzo Co., Ltd., Tokyo, Japan, to obtain transformant ST36 having a DNA encoding the present recombinant thermostable enzyme. The transformant ST36 was cultured by the method in Experiment 3-2, and the proliferated cells were collected from the resultant culture. A recombinant DNA was eluted from the cells and analyzed and revealing that it consists of about 6,700 base pairs, and, as shown in FIG. 6, it has a DNA located in the downstream of the cleavage site of Eco RV, a restriction enzyme.

EXAMPLE A-2 (b)

Preparation of recombinant thermostable enzyme from transformant

The transformant ST36 was cultured similarly as in Example A-1 except that a liquid nutrient culture medium (pH 7.0) consisting of 2 w/v % maltose, 4 w/v % "N-Z-SOY PEPTONE commercialized by Sigma Chemicals Co., St. Louis, Mo., USA, 2 w/v % yeast extract, 0.5 w/v % sodium dihydrogen phosphate, 200 μg/ml ampicillin, and water was used. The resultant culture was treated with ultrasonic to disrupt cells, and the cell suspension was centrifuged to remove insoluble substances, followed by assaying the recombinant thermostable enzyme activity in the resultant supernatant and revealing that one L culture yielded about 120,000 units of the objective recombinant thermostable enzyme. The supernatant was purified by the method in Experiment 1 to obtain an about 4,040 ml aqueous solution containing about 230 units/ml of the recombinant thermostable enzyme with a specific activity of about 80 units/mg protein.

The purified enzyme was assayed for properties and features by the method in Experiment 2 and revealing that it had a molecular weight of about 69,000–79,000 daltons on SDS-PAGE and a pI of about 5.4–6.4 on isoelectrophoresis, and was not substantially inactivated even when incubated in an aqueous solution (pH 7.0) at 85° C. for 60 min. These physicochemical properties were substantially the same as those of the enzyme from a donor microorganism of *Sulfolobus acidocaldarius* (ATCC 33909).

EXAMPLE B-1

Conversion into syrupy product containing non-reducing saccharide

Six w/w %, d.s.b., of a potato starch suspension was gelatinized by heating, adjusted to pH 4.5 and 50° C., admixed with 2,500 units/g starch, d.s.b., of an isoamylase specimen commercialized by Hayashibara Biochemical Laboratories, Inc., Okayama, Japan, and enzymatically reacted for 20 hours. The reaction mixture was adjusted to pH 6.5, autoclaved at 120° C. for 10 min to inactivate the remaining enzyme, rapidly cooled to 40° C., admixed with 150 units/g starch, d.s.b., of "TERMAMYL 60L", an α-amylase specimen commercialized by Novo Nordisk Bioindustri A/S, Copenhagen, Denmark, and enzymatically reacted for 20 hours. The reaction mixture was autoclaved at 120° C. for 20 min to inactivate the remaining enzyme, cooled to 60° C., adjusted to pH 5.5, admixed with one unit/g starch, d.s.b., of a recombinant thermostable enzyme obtained by the method in Example A-1, and enzymatically reacted for 96 hours. The resultant reaction mixture was heated at 97° C. for 30 min to inactivate the remaining enzyme, cooled and filtered, and the resultant filtrate was in usual manner decolored with an activated charcoal, desalted and purified with an ion exchanger and concentrated to obtain an about 70 w/w % syrup, d.s.b., in a yield of about 90% to the material starch, d.s.b.

The syrup had a low DE (dextrose equivalent) of 24.5 and contained 12.1 w/w % α-glucosyltrehalose, 5.4 w/w % α-maltosyltrehalose, 30.0 w/w % α-maltotriosyltrehalose, 1.4 w/w % α-maltotetraosyltrehalose and 2.0 w/w % α-maltopentaosyltrehalose. The product, having a mild and moderate sweetness as well as an adequate viscosity and moisture-retaining ability, can be satisfactorily used in composition in general such as food products, cosmetics and pharmaceuticals as a sweetener, taste-improving agent, quality-improving agent, stabilizer, filler, excipient and adjuvant.

EXAMPLE B-2

Conversion into powdery product containing non-reducing saccharide

A syrupy product containing non-reducing saccharides obtained by the method in Example B-1 was column chromatographed using a strong-acid cation exchange resin to increase the content of the non-reducing saccharides. The procedures were as follows: Four jacketed-stainless steel columns, 5.4 cm in diameter and 5 m in length each, were packed to homogeneity with "XT-1016 (Na⁺-form, polymerization degree of 4%)", a strong-acid cation exchange resin commercialized by Tokyo Organic Chemical Industries, Ltd., Tokyo, Japan, and cascaded in series to give a total column length of 20 m. The columns were fed with a syrupy product, adequately diluted with water, in a volume of about 5 v/v % to the resin and at an inner column temperature of 55° C., and fed with 55° C. hot water at an SV (space velocity ) 0.13 to elute saccharide components. Fractions rich in non-reducing saccharides were collected, pooled, concentrated, dried in vacuo and pulverized to obtain a powdery product rich in non-reducing saccharides in a yield of about 64% to the material, d.s.b.

The product had a low DE of 4.8 and contained 12.8 w/w % α-glucosyltrehalose, 11.5 w/w % α-maltosyltrehalose, 46.6 w/w % α-maltotriosyltrehalose, 2.3 w/w % α-maltotetraosyltrehalose and 3.4 w/w % α-maltopentaosyltrehalose, d.s.b. Similarly as the product in Example B-1, the product has a mild and moderate sweetness and an adequate viscosity and moisture-retaining ability, and can be satisfactorily used in compositions in general such as food products, cosmetics and pharmaceuticals as a sweetener, taste-improving agent, quality-improving agent, stabilizer, filler, excipient and adjuvant.

EXAMPLE B-3

Conversion into syrupy product containing non-reducing saccharide

To 33 w/w %, d.s.b., of corn starch suspension was added calcium carbonate to give a final concentration of 0.1 w/w %, d.s.b., adjusted to pH 6.5, and admixed with 0.2 units/g starch, d.s.b., of "TERMAMYL 60L", an α-amylase specimen commercialized by Novo Nordisk Bioindustri A/S, Copenhagen, Denmark, and enzymatically reacted at 95° C. for 15 min to liquefy the starch. The mixture was autoclaved at 120° C. for 10 min to inactivate the remaining enzyme, cooled to 55° C., admixed with 5 units/g starch, d.s.b., of a maltotetraose-forming enzyme commercialized by Hayashibara Biochemical Laboratories, Inc., Okayama, Japan, and enzymatically reacted for 6 hours. The reaction mixture was mixed with 30 units/g starch, d.s.b., of "α-amylase 2A", an α-amylase specimen commercialized by Ueda Chemical Co., Ltd., Osaka, Japan, enzymatically reacted at 65° C. for 4 hours, autoclaved at 120° C. for 10 min to inactivate the remaining enzyme, cooled to 65° C., adjusted to pH 5.5, admixed with 2 units/g starch, d.s.b., of a recombinant thermostable enzyme obtained by the method in Example A-1, and enzymatically reacted for 48 hours. The reaction mixture thus obtained was heated at 97° C. for 30 min to inactivate the remaining enzyme, cooled, filtered, decolored in usual manner with an activated charcoal, desalted and purified with ion exchangers, and concentrated to obtain an about 70 w/w % syrupy product in a yield of about 90% to the material starch, d.s.b.

The product had a low DE of 17.1 and contained 8.9 w/w % α-glucosyltrehalose, 29.3 w/w % α-maltosyltrehalose, 0.8 w/w % α-maltotriosyltrehalose, 0.7 w/w % α-maltotetraosyltrehalose and 0.7 w/w % α-maltopentaosyltrehalose, d.s.b. The product, having a mild and moderate sweetness as well as an adequate viscosity and moisture-retaining ability, can be satisfactorily used in compositions in general such as food products, cosmetics and pharmaceuticals as a sweetener, taste-improving agent, quality-improving agent, stabilizer, filler, excipient and adjuvant.

EXAMPLE B-4

Conversion into powdery product containing non-reducing saccharide

To a 20 w/w % aqueous solution containing a high-purity maltopentaose commercialized by Hayashibara Biochemical Laboratories, Inc., Okayama, Japan, was added 1.0 unit/g maltopentaose, d.s.b., of a recombinant thermostable enzyme obtained by the method in Example A-1 to effect an enzymatic reaction at 70° C. for 48 hours. A reaction mixture, wherein about 72% of the maltopentaose had been converted into α-maltotriosyltrehalose, was heated at 97° C. for 30 min to inactivate the remaining enzyme, cooled, filtered, decolored in usual manner, desalted and purified with an ion exchanger, and concentrated.

The concentrate was subjected to the same column chromatographic fractionation in Example B-1, and α-maltotriosyl rich fractions were collected, pooled, and, in usual manner, purified, concentrated and spray dried to obtain a powdery product rich in non-reducing saccharides in a yield of about 26 w/w % to the material, d.s.b.

The product, having an extremely low DE of less than 0.2 and an α-maltotriosyltrehalose content of 99.0 w/w %, d.s.b., is relatively low in sweetness, and it can be satisfactorily used in compositions in general such as food products, cosmetics and pharmaceuticals as a taste-improving agent, quality-improving agent, stabilizer, filler, excipient and adjuvant.

EXAMPLE B-5

Conversion into powdery product containing crystalline trehalose

Forty parts by weight of "PINE-DEX #4", a reducing amylaceous saccharide produced by Matsutani Chemical Ind., Co., Ltd., Kyoto, Japan, was dissolved in 60 parts by weight of water, and the solution was heated to 65° C., adjusted to pH 5.5, and admixed with one unit/g reducing amylaceous saccharide, d.s.b., of a recombinant thermostable enzyme obtained by the method in Example A-1, followed by the enzymatic reaction for 96 hours. The reaction mixture was heated at 97° C. for 30 min to inactivate the remaining enzyme, diluted up to a concentration of about 20 w/w %, d.s.b., and admixed with 10 units/g reducing amylaceous saccharide, d.s.b., of "GLUCOZYME", a glucoamylase specimen commercialized by Nagase Biochemicals, Ltd., Kyoto, Japan, followed by the enzymatic reaction for 40 hours. Thereafter, the reaction mixture was heated to inactivate the remaining enzyme, cooled, filtered, and, in usual manner, decolored with an activated charcoal, desalted and purified with an ion exchanger, and concentrated into an about 60 w/w % solution. The concentrate with a trehalose content of 30.1 w/w %, d.s.b., was subjected to column chromatographic fractionation similarly as in Example B-2 except that "CG6000", a strong-acid cation exchange resin in $Na^+$-form commercialized by Japan Organo Co., Ltd., Tokyo, Japan, was used to obtain a fraction containing about 97 w/w % trehalose, d.s.b.

The fraction was concentrated up to about 75 w/w %, d.s.b., transferred to a crystallizer, and gradually cooled while stirring to obtain a massecuite with a crystallization percentage of about 45 w/w %, d.s.b. The massecuite was sprayed downward from a nozzle equipped on the upper part of a spraying tower at a pressure of about 150 kg/cm² while an about 85° C. hot air was blowing downward from the upper part of the spraying tower, and the formed crystalline powder was collected on a wire-netting conveyer provided on the basement of the drying tower and gradually conveyed out of the spraying tower while an about 45° C. hot air was blowing to the crystalline powder from under the conveyer. The crystalline powder thus obtained was transferred to an ageing tower and aged for 10 hours in a hot air stream to complete the crystallization and drying. Thus, a powdery hydrous crystalline trehalose was obtained in a yield of about 90 w/w % to the material, d.s.b.

The product having substantial no hygroscopicity and satisfactory handleability can be suitably incorporated into compositions in general such as food products, cosmetics and pharmaceuticals as a sweetener, taste-improving agent, quality-improving agent, stabilizer, filler, excipient, and adjuvant.

EXAMPLE B-6

Conversion into syrupy product containing non-reducing saccharide

A high-purity maltotetraose commercialized by Hayashibara Biochemical Laboratories, Inc., Okayama, Japan, was dissolved in water into a 40 w/w % aqueous solution which was then mixed with 2.0 units/g maltotetraose, d.s.b., of a recombinant thermostable enzyme obtained by the method in Example A-2, and subjected to an enzymatic reaction at 60° C. for 72 hours to obtain a reaction mixture containing about 57 w/w % α-maltosyltrehalose and about 9 w/w % α-glucosyltrehalose, d.s.b. The reaction mixture was incubated at 97° C. for 30 min to inactivate the remaining enzyme, cooled, filtered in usual manner, decolored with an activated charcoal, deionized and purified with an ion exchanger, and concentrated.

The resultant concentrate was fed to a column in Example B-2, and fractions rich in α-maltosyltrehalose were collected, purified in usual manner, and concentrated to obtain an about 70 w/w % syrupy product in a yield of about 90% to the material maltotetraose, d.s.b.

The product with a low DE of 3.7, 84 w/w % α-maltosyltrehalose and 4.0 w/w % α-glucosyltrehalose, d.s.b., has a mild and high-quality sweetness and an adequate viscosity and moisture-retaining ability, and can be arbitrarily used as a sweetener, taste-improving agent, quality-improving agent, stabilizer, filler, excipient and diluent in compositions in general such as food products, cosmetics and pharmaceuticals.

As is described above, the present invention is based on the finding of a novel thermostable enzyme which forms non-reducing saccharides having a trehalose structure as an end unit from reducing amylaceous saccharides having a degree of glucose polymerization of at least 3. The present invention is to explore a way to produce such a thermostable enzyme in an industrial scale and in a relatively-high efficiency by the recombinant DNA technology. The present conversion method using the recombinant thermostable enzyme readily converts non-reducing amylaceous saccharides, having a degree of glucose polymerization of at least 3, into non-reducing saccharides having a trehalose structure as an end unit without fear of causing bacterial contamination. The non-reducing saccharides have a mild and high-quality sweetness, and, because they have no reducing residue within their molecules, they can be advantageously incorporated into compositions in general such as food products, cosmetics and pharmaceuticals without fear of causing unsatisfactory coloration and deterioration. The present recombinant thermostable enzyme is the one with a revealed amino acid sequence, so that it can be used freely in the preparations of non-reducing saccharides having a trehalose structure as an end unit which are premised to be used in food products and pharmaceuticals.

Thus, the present invention is a significant invention which exerts the aforesaid satisfactory effects and greatly contributes to this field.

While there has been described what is at present considered to be the preferred embodiments of the invention, it will be understood that various modifications may be made therein, and it is intended to cover in the appended claims all such modifications as fall within the true spirit and scope of the invention.

We claim:

1. A purified recombinant thermostable enzyme, which has the following physicochemical properties:

(1) Action

Forming non-reducing saccharides having a trehalose structure as an end unit and having a degree of glucose polymerization of at least 3 from maltotetraose or reducing amylaceous saccharides having a degree of glucose polymerization of at least 3;

(2) Molecular weight

About 69,000–79,000 daltons on sodium dodecyl sulfate polyacrylamide gel electrophoresis (SDS-PAGE);

(3) Thermostability

Substantially not inactivated even when incubated in an aqueous solution (pH 7.0) at 85° C. for 60 min.;

(4) Isolectric Point (pI)

About 5.4–6.4 on isoelectrophoresis; and (5) Amino acid sequence

An amino acid sequence which is not identical to SEQ ID NO:1 but which contains the amino acid sequences of SEQ ID NO:3 and SEQ ID NO:4.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 720 amino acids
      (B) TYPE: amino acid
      (D) TOPOLOGY: linear (ii) MOLECULE TYPE: protein (xi) SEQUENCE DESCRIPTION: SEQ ID NO:1:

```
Val Ile Ser Ala Thr Tyr Arg Leu Gln Leu Asn Lys Asn Phe Asn Phe
 1               5                  10                  15

Gly Asp Val Ile Asp Asn Leu Trp Tyr Phe Lys Asp Leu Gly Val Ser
                20                  25                  30

His Leu Tyr Leu Ser Pro Val Leu Met Ala Ser Pro Gly Ser Asn His
            35                  40                  45

Gly Tyr Asp Val Ile Asp His Ser Arg Ile Asn Asp Glu Leu Gly Gly
        50                  55                  60

Glu Lys Glu Tyr Arg Arg Leu Ile Glu Thr Ala His Thr Ile Gly Leu
```

-continued

```
                65                  70                  75                  80
Gly Ile Ile Gln Asp Ile Val Pro Asn His Met Ala Val Asn Ser Leu
                        85                  90                  95
Asn Trp Arg Leu Met Asp Val Leu Lys Met Gly Lys Lys Ser Lys Tyr
                100                 105                 110
Tyr Thr Tyr Phe Asp Phe Phe Pro Glu Asp Lys Ile Arg Leu Pro
            115                 120                 125
Ile Leu Gly Glu Asp Leu Asp Thr Val Ile Ser Lys Gly Leu Leu Lys
        130                 135                 140
Ile Val Lys Asp Gly Asp Glu Tyr Phe Leu Tyr Phe Lys Trp Lys
145                 150                 155                 160
Leu Pro Leu Thr Glu Val Gly Asn Asp Ile Tyr Asp Thr Leu Gln Lys
                165                 170                 175
Gln Asn Tyr Thr Leu Met Ser Trp Lys Asn Pro Pro Ser Tyr Arg Arg
            180                 185                 190
Phe Phe Asp Val Asn Thr Leu Ile Gly Val Asn Val Glu Lys Asp His
        195                 200                 205
Val Phe Gln Glu Ser His Ser Lys Ile Leu Asp Leu Asp Val Asp Gly
    210                 215                 220
Tyr Arg Ile Asp His Ile Asp Gly Leu Tyr Asp Pro Glu Lys Tyr Ile
225                 230                 235                 240
Asn Asp Leu Arg Ser Ile Ile Lys Asn Lys Ile Ile Val Glu Lys
                245                 250                 255
Ile Leu Gly Phe Gln Glu Glu Leu Lys Leu Asn Ser Asp Gly Thr Thr
            260                 265                 270
Gly Tyr Asp Phe Leu Asn Tyr Ser Asn Leu Leu Phe Asn Phe Asn Gln
        275                 280                 285
Glu Ile Met Asp Ser Ile Tyr Glu Asn Phe Thr Ala Glu Lys Ile Ser
    290                 295                 300
Ile Ser Glu Ser Ile Lys Lys Ile Lys Ala Gln Ile Ile Asp Glu Leu
305                 310                 315                 320
Phe Ser Tyr Glu Val Lys Arg Leu Ala Ser Gln Leu Gly Ile Ser Tyr
                325                 330                 335
Asp Ile Leu Arg Asp Tyr Leu Ser Cys Ile Asp Val Tyr Arg Thr Tyr
            340                 345                 350
Ala Asn Gln Ile Val Lys Glu Cys Asp Lys Thr Asn Glu Ile Glu Glu
        355                 360                 365
Ala Thr Lys Arg Asn Pro Glu Ala Tyr Thr Lys Leu Gln Gln Tyr Met
    370                 375                 380
Pro Ala Val Tyr Ala Lys Ala Tyr Glu Asp Thr Phe Leu Phe Arg Tyr
385                 390                 395                 400
Asn Arg Leu Ile Ser Ile Asn Glu Val Gly Ser Asp Leu Arg Tyr Tyr
                405                 410                 415
Lys Ile Ser Pro Asp Gln Phe His Val Phe Asn Gln Lys Arg Arg Gly
            420                 425                 430
Lys Ile Thr Leu Asn Ala Thr Ser Thr His Asp Thr Lys Phe Ser Glu
        435                 440                 445
Asp Val Arg Met Lys Ile Ser Val Leu Ser Glu Phe Pro Glu Glu Trp
    450                 455                 460
Lys Asn Lys Val Glu Glu Trp His Ser Ile Ile Asn Pro Lys Val Ser
465                 470                 475                 480
Arg Asn Asp Glu Tyr Arg Tyr Tyr Gln Val Leu Val Gly Ser Phe Tyr
                485                 490                 495
```

```
Glu Gly Phe Ser Asn Asp Phe Lys Glu Arg Ile Lys Gln His Met Ile
            500                 505                 510
Lys Ser Val Arg Glu Ala Lys Ile Asn Thr Ser Trp Arg Asn Gln Asn
            515                 520                 525
Lys Glu Tyr Glu Asn Arg Val Met Glu Leu Val Glu Thr Phe Thr
            530                 535                 540
Asn Lys Asp Phe Ile Lys Ser Phe Met Lys Phe Glu Ser Lys Ile Arg
545                 550                 555                 560
Arg Ile Gly Met Ile Lys Ser Leu Ser Leu Val Ala Leu Lys Ile Met
                565                 570                 575
Ser Ala Gly Ile Pro Asp Phe Tyr Gln Gly Thr Glu Ile Trp Arg Tyr
                580                 585                 590
Leu Leu Thr Asp Pro Asp Asn Arg Val Pro Val Asp Phe Lys Lys Leu
            595                 600                 605
His Glu Ile Leu Glu Lys Ser Lys Lys Phe Glu Lys Asn Met Leu Glu
            610                 615                 620
Ser Met Asp Asp Gly Arg Ile Lys Met Tyr Leu Thr Tyr Lys Leu Leu
625                 630                 635                 640
Ser Leu Arg Lys Gln Leu Ala Glu Asp Phe Leu Lys Gly Glu Tyr Lys
                645                 650                 655
Gly Leu Asp Leu Glu Glu Gly Leu Cys Gly Phe Ile Arg Phe Asn Lys
            660                 665                 670
Ile Leu Val Ile Ile Lys Thr Lys Gly Ser Val Asn Tyr Lys Leu Lys
            675                 680                 685
Leu Glu Glu Gly Ala Ile Tyr Thr Asp Val Leu Thr Gly Glu Glu Ile
            690                 695                 700
Lys Lys Glu Val Gln Ile Asn Glu Leu Pro Arg Ile Leu Val Arg Met
705                 710                 715                 720
```

(2) INFORMATION FOR SEQ ID NO:2:

(i) SEQUENCE CHARACTERISTICS:
        (A) LENGTH: 2160 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

```
GTGATATCAG CAACCTACAG ATTACAGTTA AATAAGAATT TTAATTTTGG TGACGTAATC    60

GATAACCTAT GGTATTTTAA GGATTTAGGA GTTTCCCATC TCTACCTCTC TCCTGTCTTA   120

ATGGCTTCGC CAGGAAGTAA CCATGGGTAC GATGTAATAG ATCATTCAAG GATAAACGAT   180

GAACTTGGAG GAGAGAAAGA ATACAGGAGA TTAATAGAGA CAGCTCATAC TATTGGATTA   240

GGTATTATAC AGGACATAGT ACCAAATCAC ATGGCTGTAA ATTCTCTAAA TTGGCGACTA   300

ATGGATGTAT TAAAAATGGG TAAAAGAGT AAATATTATA CGTACTTTGA CTTTTTCCCA   360

GAAGATGATA AGATACGATT ACCCATATTA GGAGAAGATT TAGATACAGT GATAAGTAAA   420

GGTTTATTAA AGATAGTAAA AGATGGAGAT GAATATTTCC TAGAATATTT CAAATGGAAA   480

CTTCCTCTAA CAGAGGTTGG AAATGATATA TACGACACTT TACAAAAACA GAATTATACC   540

CTAATGTCTT GGAAAAATCC TCCTAGCTAT AGACGATTCT TCGATGTTAA TACTTTAATA   600

GGAGTAAATG TCGAAAAAGA TCACGTATTT CAAGAGTCCC ATTCAAAGAT CTTAGATTTA   660

GATGTTGATG GCTATAGAAT TGATCATATT GATGGATTAT ATGATCCTGA GAAATATATT   720

AATGACCTGA GGTCAATAAT TAAAAATAAA ATAATTATTG TAGAAAAAAT TCTGGGATTT   780
```

```
CAGGAGGAAT TAAAATTAAA TTCAGATGGA ACTACAGGAT ATGACTTCTT AAATTACTCC        840

AACTTACTGT TTAATTTTAA TCAAGAGATA ATGGACAGTA TATATGAGAA TTTCACAGCG        900

GAGAAAATAT CTATAAGTGA AGTATAAAG AAAATAAAAG CGCAAATAAT TGATGAGCTA         960

TTTAGTTATG AAGTTAAAAG ATTAGCATCA CAACTAGGAA TTAGCTACGA TATATTGAGA       1020

GATTACCTTT CTTGTATAGA TGTGTACAGA ACTTATGCTA ATCAGATTGT AAAAGAGTGT       1080

GATAAGACCA ATGAGATAGA GGAAGCAACC AAAAGAAATC CAGAGGCTTA TACTAAATTA       1140

CAACAATATA TGCCAGCAGT ATACGCTAAA GCTTATGAAG ATACTTTCCT CTTTAGATAC       1200

AATAGATTAA TATCCATAAA TGAGGTTGGA AGCGATTTAC GATATTATAA GATATCGCCT       1260

GATCAGTTTC ATGTATTTAA TCAAAAACGA AGAGGAAAAA TCACACTAAA TGCCACTAGC       1320

ACACATGATA CTAAGTTTAG TGAAGATGTA AGGATGAAAA TAAGTGTATT AAGTGAATTT       1380

CCTGAAGAAT GGAAAAATAA GGTCGAGGAA TGGCATAGTA TCATAAATCC AAAGGTATCA       1440

AGAAATGATG AATATAGATA TTATCAGGTT TTAGTGGGAA GTTTTTATGA GGGATTCTCT       1500

AATGATTTTA AGGAGAGAAT AAAGCAACAT ATGATAAAAA GTGTCAGAGA AGCTAAGATA       1560

AATACCTCAT GGAGAAATCA AAATAAAGAA TATGAAAATA GAGTAATGGA ATTAGTGGAA       1620

GAAACTTTTA CCAATAAGGA TTTCATTAAA AGTTTCATGA AATTTGAAAG TAAGATAAGA       1680

AGGATAGGGA TGATTAAGAG CTTATCCTTG GTCGCATTAA AAATTATGTC AGCCGGTATA       1740

CCTGATTTTT ATCAGGGAAC AGAAATATGG CGATATTTAC TTACGATCC AGATAACAGA        1800

GTCCCAGTGG ATTTTAAGAA ATTACACGAA ATATTAGAAA AATCCAAAAA ATTTGAAAAA       1860

AATATGTTAG AGTCTATGGA CGATGGAAGA ATTAAGATGT ATTTAACATA TAAGCTTTTA       1920

TCCCTAAGAA AACAGTTGGC TGAGGATTTT TTAAAGGGCG AGTATAAGGG ATTAGATCTA       1980

GAAGAAGGAC TATGTGGGTT TATTAGGTTT AACAAAATTT TGGTAATAAT AAAAACCAAG       2040

GGAAGTGTTA ATTACAAACT GAAACTTGAA GAGGGAGCAA TTTACACAGA TGTATTGACA       2100

GGAGAAGAAA TTAAAAAAGA GGTACAGATT AATGAGCTAC CTAGGATACT AGTTAGAATG       2160
```

(2) INFORMATION FOR SEQ ID NO:3:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Ile Ser Ala Thr Tyr Arg Leu Gln Leu Asn Lys Asn Phe Asn Phe
1               5                  10                  15

Gly Asp Val Ile Asp Asn Leu Trp Tyr Phe Lys Asp Leu Gly
            20                  25                  30
```

(2) INFORMATION FOR SEQ ID NO:4:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Val Glu Glu Trp His Ser Ile Ile Asn Pro Lys (2) INFORMATION FOR SEQ ID NO:5:

(i) SEQUENCE CHARACTERISTICS:
        (A) LENGTH: 2160 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
GTG ATA TCA GCA ACC TAC AGA TTA CAG TTA AAT AAG AAT TTT AAT TTT      48
Val Ile Ser Ala Thr Tyr Arg Leu Gln Leu Asn Lys Asn Phe Asn Phe
 1               5                   10                  15

GGT GAC GTA ATC GAT AAC CTA TGG TAT TTT AAG GAT TTA GGA GTT TCC      96
Gly Asp Val Ile Asp Asn Leu Trp Tyr Phe Lys Asp Leu Gly Val Ser
                20                  25                  30

CAT CTC TAC CTC TCT CCT GTC TTA ATG GCT TCG CCA GGA AGT AAC CAT     144
His Leu Tyr Leu Ser Pro Val Leu Met Ala Ser Pro Gly Ser Asn His
            35                  40                  45

GGG TAC GAT GTA ATA GAT CAT TCA AGG ATA AAC GAT GAA CTT GGA GGA     192
Gly Tyr Asp Val Ile Asp His Ser Arg Ile Asn Asp Glu Leu Gly Gly
        50                  55                  60

GAG AAA GAA TAC AGG AGA TTA ATA GAG ACA GCT CAT ACT ATT GGA TTA     240
Glu Lys Glu Tyr Arg Arg Leu Ile Glu Thr Ala His Thr Ile Gly Leu
65                  70                  75                  80

GGT ATT ATA CAG GAC ATA GTA CCA AAT CAC ATG GCT GTA AAT TCT CTA     288
Gly Ile Ile Gln Asp Ile Val Pro Asn His Met Ala Val Asn Ser Leu
                85                  90                  95

AAT TGG CGA CTA ATG GAT GTA TTA AAA ATG GGT AAA AAG AGT AAA TAT     336
Asn Trp Arg Leu Met Asp Val Leu Lys Met Gly Lys Lys Ser Lys Tyr
            100                 105                 110

TAT ACG TAC TTT GAC TTT TTC CCA GAA GAT GAT AAG ATA CGA TTA CCC     384
Tyr Thr Tyr Phe Asp Phe Phe Pro Glu Asp Asp Lys Ile Arg Leu Pro
        115                 120                 125

ATA TTA GGA GAA GAT TTA GAT ACA GTG ATA AGT AAA GGT TTA TTA AAG     432
Ile Leu Gly Glu Asp Leu Asp Thr Val Ile Ser Lys Gly Leu Leu Lys
130                 135                 140

ATA GTA AAA GAT GGA GAT GAA TAT TTC CTA GAA TAT TTC AAA TGG AAA     480
Ile Val Lys Asp Gly Asp Glu Tyr Phe Leu Glu Tyr Phe Lys Trp Lys
145                 150                 155                 160

CTT CCT CTA ACA GAG GTT GGA AAT GAT ATA TAC GAC ACT TTA CAA AAA     528
Leu Pro Leu Thr Glu Val Gly Asn Asp Ile Tyr Asp Thr Leu Gln Lys
                165                 170                 175

CAG AAT TAT ACC CTA ATG TCT TGG AAA AAT CCT CCT AGC TAT AGA CGA     576
Gln Asn Tyr Thr Leu Met Ser Trp Lys Asn Pro Pro Ser Tyr Arg Arg
            180                 185                 190

TTC TTC GAT GTT AAT ACT TTA ATA GGA GTA AAT GTC GAA AAA GAT CAC     624
Phe Phe Asp Val Asn Thr Leu Ile Gly Val Asn Val Glu Lys Asp His
        195                 200                 205

GTA TTT CAA GAG TCC CAT TCA AAG ATC TTA GAT TTA GAT GTT GAT GGC     672
Val Phe Gln Glu Ser His Ser Lys Ile Leu Asp Leu Asp Val Asp Gly
210                 215                 220

TAT AGA ATT GAT CAT ATT GAT GGA TTA TAT GAT CCT GAG AAA TAT ATT     720
Tyr Arg Ile Asp His Ile Asp Gly Leu Tyr Asp Pro Glu Lys Tyr Ile
225                 230                 235                 240

AAT GAC CTG AGG TCA ATA ATT AAA AAT AAA ATA ATT GTA GAA AAA         768
Asn Asp Leu Arg Ser Ile Ile Lys Asn Lys Ile Ile Val Glu Lys
                245                 250                 255

ATT CTG GGA TTT CAG GAG GAA TTA AAA TTA AAT TCA GAT GGA ACT ACA     816
```

```
Ile Leu Gly Phe Gln Glu Glu Leu Lys Leu Asn Ser Asp Gly Thr Thr
            260                 265                 270

GGA TAT GAC TTC TTA AAT TAC TCC AAC TTA CTG TTT AAT TTT AAT CAA      864
Gly Tyr Asp Phe Leu Asn Tyr Ser Asn Leu Leu Phe Asn Phe Asn Gln
            275                 280                 285

GAG ATA ATG GAC AGT ATA TAT GAG AAT TTC ACA GCG GAG AAA ATA TCT      912
Glu Ile Met Asp Ser Ile Tyr Glu Asn Phe Thr Ala Glu Lys Ile Ser
            290                 295                 300

ATA AGT GAA AGT ATA AAG AAA ATA AAA GCG CAA ATA ATT GAT GAG CTA      960
Ile Ser Glu Ser Ile Lys Lys Ile Lys Ala Gln Ile Ile Asp Glu Leu
305                 310                 315                 320

TTT AGT TAT GAA GTT AAA AGA TTA GCA TCA CAA CTA GGA ATT AGC TAC     1008
Phe Ser Tyr Glu Val Lys Arg Leu Ala Ser Gln Leu Gly Ile Ser Tyr
                325                 330                 335

GAT ATA TTG AGA GAT TAC CTT TCT TGT ATA GAT GTG TAC AGA ACT TAT     1056
Asp Ile Leu Arg Asp Tyr Leu Ser Cys Ile Asp Val Tyr Arg Thr Tyr
            340                 345                 350

GCT AAT CAG ATT GTA AAA GAG TGT GAT AAG ACC AAT GAG ATA GAG GAA     1104
Ala Asn Gln Ile Val Lys Glu Cys Asp Lys Thr Asn Glu Ile Glu Glu
            355                 360                 365

GCA ACC AAA AGA AAT CCA GAG GCT TAT ACT AAA TTA CAA CAA TAT ATG     1152
Ala Thr Lys Arg Asn Pro Glu Ala Tyr Thr Lys Leu Gln Gln Tyr Met
370                 375                 380

CCA GCA GTA TAC GCT AAA GCT TAT GAA GAT ACT TTC CTC TTT AGA TAC     1200
Pro Ala Val Tyr Ala Lys Ala Tyr Glu Asp Thr Phe Leu Phe Arg Tyr
385                 390                 395                 400

AAT AGA TTA ATA TCC ATA AAT GAG GTT GGA AGC GAT TTA CGA TAT TAT     1248
Asn Arg Leu Ile Ser Ile Asn Glu Val Gly Ser Asp Leu Arg Tyr Tyr
                405                 410                 415

AAG ATA TCG CCT GAT CAG TTT CAT GTA TTT AAT CAA AAA CGA AGA GGA     1296
Lys Ile Ser Pro Asp Gln Phe His Val Phe Asn Gln Lys Arg Arg Gly
            420                 425                 430

AAA ATC ACA CTA AAT GCC ACT AGC ACA CAT GAT ACT AAG TTT AGT GAA     1344
Lys Ile Thr Leu Asn Ala Thr Ser Thr His Asp Thr Lys Phe Ser Glu
            435                 440                 445

GAT GTA AGG ATG AAA ATA AGT GTA TTA AGT GAA TTT CCT GAA GAA TGG     1392
Asp Val Arg Met Lys Ile Ser Val Leu Ser Glu Phe Pro Glu Glu Trp
            450                 455                 460

AAA AAT AAG GTC GAG GAA TGG CAT AGT ATC ATA AAT CCA AAG GTA TCA     1440
Lys Asn Lys Val Glu Glu Trp His Ser Ile Ile Asn Pro Lys Val Ser
465                 470                 475                 480

AGA AAT GAT GAA TAT AGA TAT TAT CAG GTT TTA GTG GGA AGT TTT TAT     1488
Arg Asn Asp Glu Tyr Arg Tyr Tyr Gln Val Leu Val Gly Ser Phe Tyr
                485                 490                 495

GAG GGA TTC TCT AAT GAT TTT AAG GAG AGA ATA AAG CAA CAT ATG ATA     1536
Glu Gly Phe Ser Asn Asp Phe Lys Glu Arg Ile Lys Gln His Met Ile
            500                 505                 510

AAA AGT GTC AGA GAA GCT AAG ATA AAT ACC TCA TGG AGA AAT CAA AAT     1584
Lys Ser Val Arg Glu Ala Lys Ile Asn Thr Ser Trp Arg Asn Gln Asn
            515                 520                 525

AAA GAA TAT GAA AAT AGA GTA ATG GAA TTA GTG GAA GAA ACT TTT ACC     1632
Lys Glu Tyr Glu Asn Arg Val Met Glu Leu Val Glu Glu Thr Phe Thr
            530                 535                 540

AAT AAG GAT TTC ATT AAA AGT TTC ATG AAA TTT GAA AGT AAG ATA AGA     1680
Asn Lys Asp Phe Ile Lys Ser Phe Met Lys Phe Glu Ser Lys Ile Arg
545                 550                 555                 560

AGG ATA GGG ATG ATT AAG AGC TTA TCC TTG GTC GCA TTA AAA ATT ATG     1728
Arg Ile Gly Met Ile Lys Ser Leu Ser Leu Val Ala Leu Lys Ile Met
                565                 570                 575

TCA GCC GGT ATA CCT GAT TTT TAT CAG GGA ACA GAA ATA TGG CGA TAT     1776
```

```
Ser Ala Gly Ile Pro Asp Phe Tyr Gln Gly Thr Glu Ile Trp Arg Tyr
            580                 585                 590

TTA CTT ACA GAT CCA GAT AAC AGA GTC CCA GTG GAT TTT AAG AAA TTA    1824
Leu Leu Thr Asp Pro Asp Asn Arg Val Pro Val Asp Phe Lys Lys Leu
        595                 600                 605

CAC GAA ATA TTA GAA AAA TCC AAA AAA TTT GAA AAA AAT ATG TTA GAG    1872
His Glu Ile Leu Glu Lys Ser Lys Lys Phe Glu Lys Asn Met Leu Glu
    610                 615                 620

TCT ATG GAC GAT GGA AGA ATT AAG ATG TAT TTA ACA TAT AAG CTT TTA    1920
Ser Met Asp Asp Gly Arg Ile Lys Met Tyr Leu Thr Tyr Lys Leu Leu
625                 630                 635                 640

TCC CTA AGA AAA CAG TTG GCT GAG GAT TTT TTA AAG GGC GAG TAT AAG    1968
Ser Leu Arg Lys Gln Leu Ala Glu Asp Phe Leu Lys Gly Glu Tyr Lys
                645                 650                 655

GGA TTA GAT CTA GAA GAA GGA CTA TGT GGG TTT ATT AGG TTT AAC AAA    2016
Gly Leu Asp Leu Glu Glu Gly Leu Cys Gly Phe Ile Arg Phe Asn Lys
            660                 665                 670

ATT TTG GTA ATA ATA AAA ACC AAG GGA AGT GTT AAT TAC AAA CTG AAA    2064
Ile Leu Val Ile Ile Lys Thr Lys Gly Ser Val Asn Tyr Lys Leu Lys
        675                 680                 685

CTT GAA GAG GGA GCA ATT TAC ACA GAT GTA TTG ACA GGA GAA GAA ATT    2112
Leu Glu Glu Gly Ala Ile Tyr Thr Asp Val Leu Thr Gly Glu Glu Ile
    690                 695                 700

AAA AAA GAG GTA CAG ATT AAT GAG CTA CCT AGG ATA CTA GTT AGA ATG    2160
Lys Lys Glu Val Gln Ile Asn Glu Leu Pro Arg Ile Leu Val Arg Met
705                 710                 715                 720
```

(2) INFORMATION FOR SEQ ID NO:6:

(i) SEQUENCE CHARACTERISTICS:
        (A) LENGTH: 222 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
GATCCGTTCT GGCAAATATT CTGAAATGAG CTGTTGACAA TTAATCATCG GCTCGTCTAA    60

TGTGTGGAAT TCTGATTCGA ATTTTTTAAT AAAATCAGGA GGAAAAAATA TGATATCAGC   120

AACCTACAGA TTACAGTTAA ATAAGAATTT TAATTTTGGT GACGTAATCG ATGAATTCAC   180

TAGTTAGAAT GTGATGAAGG CCTGCGGCCG CTGCAGAGCT CA                      222
```

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
AAYYTNTGGT AYTTYAARGA                                                20
```

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GARGARTGGC AYWSNATHAT                                          20

(2) INFORMATION FOR SEQ ID NO:9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GATCCGTTCT GGCAAATATT CTGAAATGAG CTGT                           34

(2) INFORMATION FOR SEQ ID NO:10:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

TGACAATTAA TCATCGGCTC GTCTAATGTG TGGAATTCTG ATTCGA              46

(2) INFORMATION FOR SEQ ID NO:11:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

ATTTTTTAAT AAAATCAGGA GGAAAAAATA TGATATCAGC AACCTACA            48

(2) INFORMATION FOR SEQ ID NO:12:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GATTACAGTT AAATAAGAAT TTTAATTTTG GTGACGTAAT CGATGAA             47

(2) INFORMATION FOR SEQ ID NO:13:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

TTCACTAGTT AGAATGTGAT GAAGGCCTGC GGCCGCTGCA GAGCTCA             47

(2) INFORMATION FOR SEQ ID NO:14:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CGATGATTAA TTGTCAACAG CTCATTTCAG AATATTTGCC AGAAGC           46

(2) INFORMATION FOR SEQ ID NO:15:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

TTTTATTAAA AAATTCGAAT CAGAATTCCA CACATTAGAC GAGC             44

(2) INFORMATION FOR SEQ ID NO:16:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

TTAACTGTAA TCTGTAGGTT GCTGATATCA TATTTTTTCC TCCTGA           46

(2) INFORMATION FOR SEQ ID NO:17:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TAGTGAATTC TACGATTACG TCACCAAAAT TAAAATTCTT AT               42

(2) INFORMATION FOR SEQ ID NO:18:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

AGCTTGAGCT CTGCAGCGGC CGCAGGCCTT CATCACATTC TAAC             44

(2) INFORMATION FOR SEQ ID NO:19:

(i) SEQUENCE CHARACTERISTICS:

-continued

```
   (A) LENGTH: 17 base pairs
   (B) TYPE: nucleic acid
   (C) STRANDEDNESS: single
   (D) TOPOLOGY: linear (ii) MOLECULE TYPE: cDNA (xi) SEQUENCE DESCRIPTION: SEQ ID NO:19:

GTAAAACGAC GGCCAGT                                                   17
```